United States Patent
Rochais

(10) Patent No.: US 12,064,470 B2
(45) Date of Patent: Aug. 20, 2024

(54) FGF10 FOR THE TREATMENT OF HEART DISEASES

(71) Applicants: UNIVERSITE D'AIX-MARSEILLE, Marseilles (FR); INSERM (INSTITUT NATIONAL DE LA SANTÉ ET DE LA RECHERCHE MÉDICALE), Paris (FR)

(72) Inventor: Francesca Nadège Joëlle Rochais, Le Beausset (FR)

(73) Assignees: UNIVERSITE D'AIX-MARSEILLE, Marseilles (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 81 days.

(21) Appl. No.: 16/764,043

(22) PCT Filed: Nov. 16, 2018

(86) PCT No.: PCT/EP2018/081584
§ 371 (c)(1),
(2) Date: May 14, 2020

(87) PCT Pub. No.: WO2019/097001
PCT Pub. Date: May 23, 2019

(65) Prior Publication Data
US 2020/0276268 A1    Sep. 3, 2020

(30) Foreign Application Priority Data

Nov. 16, 2017   (EP) ..................... 17306594

(51) Int. Cl.
*A61K 38/18*   (2006.01)
(52) U.S. Cl.
CPC ................. *A61K 38/1825* (2013.01)
(58) Field of Classification Search
None
See application file for complete search history.

(56) References Cited

U.S. PATENT DOCUMENTS

| | | | | |
|---|---|---|---|---|
| 8,236,527 B2 * | 8/2012 | Chen | ..................... | C07K 14/495 435/69.1 |
| 2005/0019824 A1 * | 1/2005 | Alderson | ............... | C07K 14/50 435/325 |
| 2005/0261189 A1 * | 11/2005 | Larsen | ................ | C07K 14/475 514/8.5 |
| 2007/0071675 A1 | 3/2007 | Wu et al. | | |

FOREIGN PATENT DOCUMENTS

| | | |
|---|---|---|
| GB | 2332373 A * | 6/1999 |
| WO | WO 00/38518 | 7/2000 |

OTHER PUBLICATIONS

Itoh, N. "FGF10: A multifunctional mesenchymal-epithelial signaling growth factor in development, health, and disease" *Cytokine & Growth Factor Reviews*, Oct. 31, 2015, pp. 63-69, vol. 28.
Itoh, N. et al. "Roles of FGF Signals in Heart Development, Health, and Disease" *Frontiers in Cell and Developmental Biology*, Oct. 18, 2016, pp. 1-11, vol. 4, Article 110.
Payan, S. et al. "From heart development to cardiac regeneration: role of the Fibroblast Growth Factor FGF10" *Archives of Cardiovascular Diseases Supplements*, Mar. 20, 2017, p. 173, vol. 9, No. 2.
Rochais, F. et al. "FGF10 promotes regional foetal cardiomyocyte proliferation and adult cardiomyocyte cell-cycle re-entry" *Cardiovascular Research*, 2014, pp. 432-442, vol. 104, No. 3.
Written Opinion in International Application No. PCT/EP2018/081584, Mar. 7, 2019, pp. 1-10.
Anonymous, "Rodent Myocardial Infarction Models" *Creative Biolabs*, 2023, pp. 1-7.
Zhang, X. et al. "Receptor Specificity of the Fibroblast Growth Factor Family, The Complete Mammalian FGF Family" *the Journal of Biological Chemistry*, Jun. 9, 2006, pp. 15694-15700, vol. 281, No. 23.
Rubin, N. et al. "FGF10 Signaling Enhances Epicardial Cell Expansion during Neonatal Mouse Heart Repair" *J Cardiovasc Dis Diagn.*, Mar. 2013, pp. 1-20, vol. 1, No. 1.
Wang, Y. et al. "Preclinical rodent models of cardiac fibrosis" *Br J Pharmacol.*, 2022, pp. 882-899, vol. 179.
Antoine. M. et al. "Expression pattern of fibroblast growth factors (FGFs), their receptors and antagonists in primary endothelial cells and vascular smooth muscle cells" *Growth Factors*, 2005, pp. 87-95, vol. 23, No. 2.
Riehle, C. et al. "Small animal models of heart failure" *Cardiovascular Research*, 2019, pp. 1838-1849, vol. 115.
Gyöngyösi, M. et al. "Myocardial fibrosis: biomedical research from bench to bedside" *European Journal of Heart Failure*, 2017, pp. 177-191, vol. 19.

* cited by examiner

*Primary Examiner* — Marianne P Allen
(74) *Attorney, Agent, or Firm* — SALIWANCHIK, LLOYD & EISENSCHENK

(57) ABSTRACT

The present invention relates to the activation of FGF10 signaling pathway for use in the treatment of a heart disease.

Figure 1:
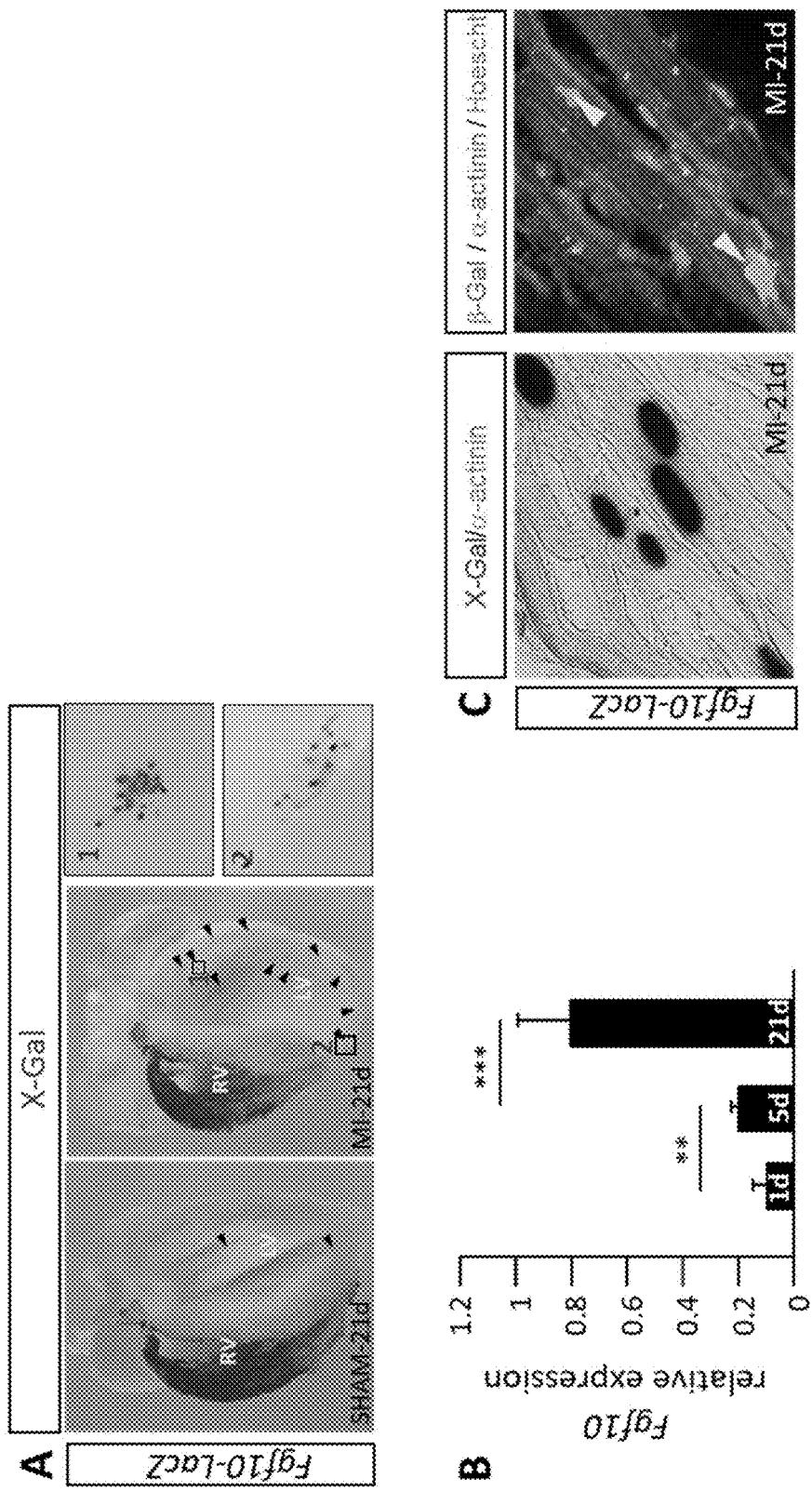

12 Claims, 17 Drawing Sheets
Specification includes a Sequence Listing.

SEQUENCE LISTING

```
<160> NUMBER OF SEQ ID NOS: 38

<210> SEQ ID NO 1
<211> LENGTH: 27
<212> TYPE: DNA
<213> ORGANISM: artificial
<220> FEATURE:
<223> OTHER INFORMATION: primer

<400> SEQUENCE: 1
cttccagtat gttccttctg atgagac                                       27

<210> SEQ ID NO 2
<211> LENGTH: 25
<212> TYPE: DNA
<213> ORGANISM: artificial
<220> FEATURE:
<223> OTHER INFORMATION: primer

<400> SEQUENCE: 2
tacggacagt cttcttcttg gtccc                                         25

<210> SEQ ID NO 3
<211> LENGTH: 30
<212> TYPE: DNA
<213> ORGANISM: artificial
<220> FEATURE:
<223> OTHER INFORMATION: primer

<400> SEQUENCE: 3
gagcttgctg ggggaaactt cctgactagg                                    30

<210> SEQ ID NO 4
<211> LENGTH: 20
<212> TYPE: DNA
<213> ORGANISM: artificial
```

```
<220> FEATURE:
<223> OTHER INFORMATION: primer

<400> SEQUENCE: 4
atcctctgca tggtcaggtc                                               20

<210> SEQ ID NO 5
<211> LENGTH: 18
<212> TYPE: DNA
<213> ORGANISM: artificial
<220> FEATURE:
<223> OTHER INFORMATION: primer

<400> SEQUENCE: 5
cgtggcctga ttcattcc                                                 18

<210> SEQ ID NO 6
<211> LENGTH: 23
<212> TYPE: DNA
<213> ORGANISM: artificial
<220> FEATURE:
<223> OTHER INFORMATION: primer

<400> SEQUENCE: 6
aagtcgctct gagttgttat cag                                           23

<210> SEQ ID NO 7
<211> LENGTH: 22
<212> TYPE: DNA
<213> ORGANISM: artificial
<220> FEATURE:
<223> OTHER INFORMATION: primer

<400> SEQUENCE: 7
ggagcgggag aaatggatat ga                                            22

<210> SEQ ID NO 8
<211> LENGTH: 24
<212> TYPE: DNA
<213> ORGANISM: artificial
<220> FEATURE:
<223> OTHER INFORMATION: primer

<400> SEQUENCE: 8
cgggttgtta aaccttcgat tccg                                          24

<210> SEQ ID NO 9
<211> LENGTH: 17
<212> TYPE: DNA
<213> ORGANISM: artificial
<220> FEATURE:
<223> OTHER INFORMATION: primer

<400> SEQUENCE: 9
gacgccatcc acgctgt                                                  17

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
tgctgccagt taaaagatgc                                               20
```

```
<210> SEQ ID NO 11
<211> LENGTH: 23
<212> TYPE: DNA
<213> ORGANISM: artificial
<220> FEATURE:
<223> OTHER INFORMATION: primer

<400> SEQUENCE: 11
caacacagat ctgatggatt tca                                              23

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
cctcatcttc taccggcatc                                                  20

<210> SEQ ID NO 13
<211> LENGTH: 21
<212> TYPE: DNA
<213> ORGANISM: artificial
<220> FEATURE:
<223> OTHER INFORMATION: primer

<400> SEQUENCE: 13
gtcagtcgtt tgggctgtaa c                                                21

<210> SEQ ID NO 14
<211> LENGTH: 20
<212> TYPE: DNA
<213> ORGANISM: artificial
<220> FEATURE:
<223> OTHER INFORMATION: primer

<400> SEQUENCE: 14
agacccaggc agagtcagaa                                                  20

<210> SEQ ID NO 15
<211> LENGTH: 21
<212> TYPE: DNA
<213> ORGANISM: artificial
<220> FEATURE:
<223> OTHER INFORMATION: primer

<400> SEQUENCE: 15
catgttcagc tttgtggacc t                                                21

<210> SEQ ID NO 16
<211> LENGTH: 20
<212> TYPE: DNA
<213> ORGANISM: artificial
<220> FEATURE:
<223> OTHER INFORMATION: primer

<400> SEQUENCE: 16
gcagctgact tcagggatgt                                                  20

<210> SEQ ID NO 17
<211> LENGTH: 19
<212> TYPE: DNA
<213> ORGANISM: artificial
<220> FEATURE:
<223> OTHER INFORMATION: primer
```

```
<400> SEQUENCE: 17
tggtcctgct ggaaaggat                                           19

<210> SEQ ID NO 18
<211> LENGTH: 18
<212> TYPE: DNA
<213> ORGANISM: artificial
<220> FEATURE:
<223> OTHER INFORMATION: primer

<400> SEQUENCE: 18
gaggtccagg cagtccac                                            18

<210> SEQ ID NO 19
<211> LENGTH: 20
<212> TYPE: DNA
<213> ORGANISM: artificial
<220> FEATURE:
<223> OTHER INFORMATION: primer

<400> SEQUENCE: 19
gagaagaacg gcaaggtcag                                          20

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
tttccccttc ttgttcatgg                                          20

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
ctggtgaaaa ggacctctcg                                          20

<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
tggcaacatc aacaggactc                                          20

<210> SEQ ID NO 23
<211> LENGTH: 20
<212> TYPE: DNA
<213> ORGANISM: artificial
<220> FEATURE:
<223> OTHER INFORMATION: primer

<400> SEQUENCE: 23
aactaacccg ggacttggag                                          20

<210> SEQ ID NO 24
```

```
<211> LENGTH: 20
<212> TYPE: DNA
<213> ORGANISM: artificial
<220> FEATURE:
<223> OTHER INFORMATION: primer

<400> SEQUENCE: 24
agtagaactc gggcaagctg                                              20

<210> SEQ ID NO 25
<211> LENGTH: 20
<212> TYPE: DNA
<213> ORGANISM: artificial
<220> FEATURE:
<223> OTHER INFORMATION: primer

<400> SEQUENCE: 25
cctcaagctc atggctacac                                              20

<210> SEQ ID NO 26
<211> LENGTH: 20
<212> TYPE: DNA
<213> ORGANISM: artificial
<220> FEATURE:
<223> OTHER INFORMATION: primer

<400> SEQUENCE: 26
ttgcctcctt tgcctttacc                                              20

<210> SEQ ID NO 27
<211> LENGTH: 20
<212> TYPE: DNA
<213> ORGANISM: artificial
<220> FEATURE:
<223> OTHER INFORMATION: primer

<400> SEQUENCE: 27
aggcaaagaa aggctcatcc                                              20

<210> SEQ ID NO 28
<211> LENGTH: 20
<212> TYPE: DNA
<213> ORGANISM: artificial
<220> FEATURE:
<223> OTHER INFORMATION: primer

<400> SEQUENCE: 28
tggagcgcaa gtttgtcata                                              20

<210> SEQ ID NO 29
<211> LENGTH: 21
<212> TYPE: DNA
<213> ORGANISM: artificial
<220> FEATURE:
<223> OTHER INFORMATION: primer

<400> SEQUENCE: 29
agcctcttct cattcctgct t                                            21

<210> SEQ ID NO 30
<211> LENGTH: 19
<212> TYPE: DNA
<213> ORGANISM: artificial
<220> FEATURE:
<223> OTHER INFORMATION: primer

<400> SEQUENCE: 30
```

-continued atgagaggga ggccatttg                                              19

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31
ctcgctcagc accttctctc                                             20

<210> SEQ ID NO 32
<211> LENGTH: 19
<212> TYPE: DNA
<213> ORGANISM: artificial
<220> FEATURE:
<223> OTHER INFORMATION: primer

<400> SEQUENCE: 32
cactctgggt ggctgagtc                                              19

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
gaaggagaac tgcccgtaca                                             20

<210> SEQ ID NO 34
<211> LENGTH: 22
<212> TYPE: DNA
<213> ORGANISM: artificial
<220> FEATURE:
<223> OTHER INFORMATION: primer

<400> SEQUENCE: 34
ggcaacaact ccgatttcta ct                                          22

<210> SEQ ID NO 35
<211> LENGTH: 20
<212> TYPE: DNA
<213> ORGANISM: artificial
<220> FEATURE:
<223> OTHER INFORMATION: primer

<400> SEQUENCE: 35
atgctggacc caacacaaat                                             20

<210> SEQ ID NO 36
<211> LENGTH: 21
<212> TYPE: DNA
<213> ORGANISM: artificial
<220> FEATURE:
<223> OTHER INFORMATION: primer

<400> SEQUENCE: 36
tctttcactt tgccaaacac c                                           21

<210> SEQ ID NO 37
<211> LENGTH: 20
<212> TYPE: DNA

```
<213> ORGANISM: artificial
<220> FEATURE:
<223> OTHER INFORMATION: primer

<400> SEQUENCE: 37
gtggacatcg gatacccaag                                                 20

<210> SEQ ID NO 38
<211> LENGTH: 20
<212> TYPE: DNA
<213> ORGANISM: artificial
<220> FEATURE:
<223> OTHER INFORMATION: primer

<400> SEQUENCE: 38
aagttggaag gccggttaat                                                 20
```

FGF10 FOR THE TREATMENT OF HEART DISEASES

CROSS-REFERENCE TO RELATED APPLICATION

This application is the U.S. national stage application of International Patent Application No. PCT/EP2018/081584, filed Nov. 16, 2018.

The Sequence Listing for this application is labeled "Seq-List.txt" which was created on May 11, 2020 and is 6653 bytes. The entire content of the sequence listing is incorporated herein by reference in its entirety.

FIELD OF THE INVENTION

The present invention relates to FGF10 for use in the treatment of heart diseases.

BACKGROUND OF THE INVENTION

Cardiovascular diseases are the leading cause of mortality, accounting for 33% of all deaths in the United States in 2008 and 29% in France. In 2008, the annual economic cost of cardiovascular diseases in the United States was an estimated at 297.7 billion dollars which accounted for 16% of total health expenditure, clearly demonstrating that cardiovascular diseases are a major public health problem in industrialized countries. Cardiac diseases including myocardial infarction are characterized by cardiomyocyte loss which leads to dramatic impairment of cardiac function and ultimately to congestive heart failure. Despite significant advances, conventional treatments do not correct the defects in cardiac muscle cell numbers and the prognosis of congestive heart failure remains poor. Specific needs remain for new strategies to enhance cardiac regeneration and to replace cardiomyocytes following cardiac injury and disease. The existence, in adult mammalian heart, of low but detectable cardiomyocyte proliferative capacities (Bergmann O, et al. (2009), Science, 324:98-102) has shifted the target of regenerative therapy toward new therapeutical strategies that aims to the promotion of mature cardiomyocyte cell cycle re-entry. Recent evidence showing that mammalian cardiomyocyte renewal potential is lost shortly after birth strongly supports the hypothesis that a detailed understanding of the regulation of fetal cardiomyocyte proliferation is essential to identify targets for cardiac repair and regeneration in congenital and acquired heart disease.

However, to date, no efficient treatment aiming to promote mature cardiomyocyte cell cycle re-entry is currently available.

The inventors have recently uncovered a role for FGF10 signaling in regulating both fetal and adult cardiomyocyte proliferation (Rochais F, et al. 2014, Cardiovasc Res, 104: 432-42). The role of Fgf10 in controlling fetal cardiomyocyte proliferation was uncovered using heart sections and cardiac cell primary cultures arising from wildtype and Fgf10 knock-out embryos. Furthermore, using an inducible transgenic mouse model, Fgf10 overexpression led to an increase in cardiomyocyte proliferation. However, this study did not investigate the role of FGF10 in the pathogenesis of heart diseases, in particular myocardial infarction. It was thus not certain that FGF10 was actually a target of choice for the treatment of heart diseases.

SUMMARY OF THE INVENTION

Unexpectedly, it is herein shown, using a mouse model of myocardial infarction that FGF10 specifically promotes cardiomyocyte proliferation after myocardial infarction, leading to cardiac regeneration. In addition the results show that FGF10 is also required to prevent cardiac fibrosis infiltration and to repress prolonged inflammation, both parameters strongly participating to the deleterious cardiac remodeling post-infarction, thus demonstrating that FGF10 is crucial for cardiac repair in pathological conditions. Finally, the presented results clearly demonstrate that FGF10 is required to preserve cardiac performance following myocardial infarction. Thus this is the first report showing the protective effect of FGF10 signaling pathway in the context of heart diseases. The invention thus provides a potent strategy for the treatment of heart diseases including myocardial infarction.

Accordingly, the present invention relates to FGF10, a vector encoding FGF10, or an activator of FGF10 signaling pathway, for use in a method for treating a heart disease.

In particular, FGF10, or a vector encoding the same, or an activator of FGF10 signaling pathway, is used to enhance cardiac repair and regeneration (replacement of damaged cardiomyocytes) in particular a patient displaying a heart disease such as myocardial infarction and ischemic heart disease (e.g. chronic ischemic heart disease). Thanks to the invention, FGF10, or a nucleic acid encoding the same, or an activator of FGF10 signaling pathway, may be used to repair and/or regenerate cardiac tissue of said patient. In another embodiment, the invention provides FGF10, or a vector encoding the same, or an activator of FGF10 signaling pathway, for use in the prevention of congestive heart failure.

LEGENDS OF THE FIGURES

FIG. 1: Fgf10 expression is upregulated in cardiomyocytes after myocardial infarction. (A) Whole mount view of half heart from sham-operated (SHAM) and myocardial infracted (MI) Fgf10-LacZ mice, 21 days (21 d) post-MI, showing X-gal$^+$ cells (arrowheads). (B) qRT-PCR experiment on left ventricular MI hearts showing increased Fgf10 expression at 1 day (1 d), 5 days (5 d) and 21 days (21 d) after MI. (C) Cryostat sections of Fgf10-LacZ-MI hearts showing X-gal$^+$ nuclei (arrowhead) in cardiomyocytes (α-actinin-expressing cells). , $0,001<p<0.01$; *, $p<0.001$; Student's t-test.

Figure 2:
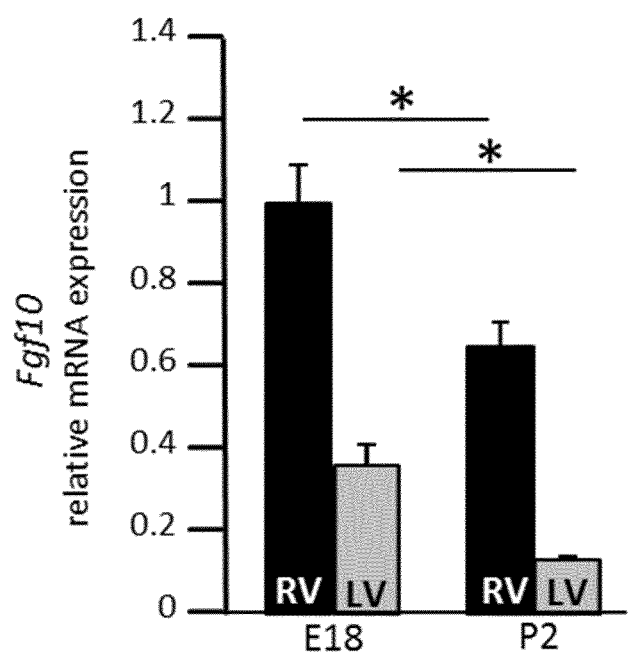

FIG. 2: Decreased Fgf10 expression after birth correlates with the loss of regenerative capacities. qRT-PCR experiments on right and left ventricular tissues from fetal (E18) and postnatal (P2) wildtype mice. Right ventricle (RV), left ventricle (LV). *, $p<0.05$; Student's t-test.

Figure 3:
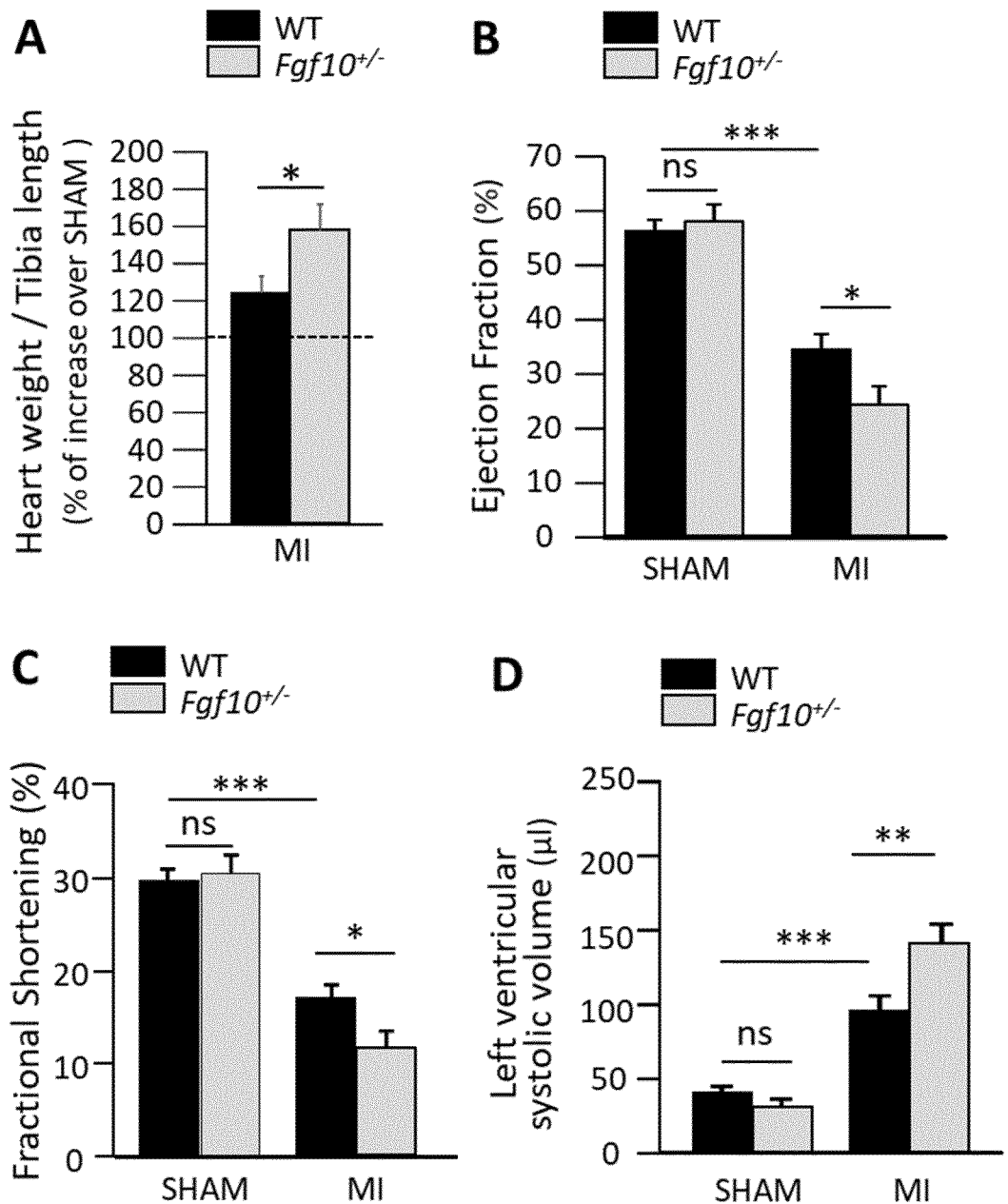

FIG. 3: Decreased Fgf10 dosage worsens heart remodeling and cardiac function following myocardial infarction. WT and Fgf10$^{+/-}$ adult mice were subjected to myocardial infarction. Three weeks after the surgery, heart weight/tibia length ratio was measured (A) and ejection fraction (B), fractional shortening (C) and left ventricular diastolic volume (D) were assessed using echocardiography (CERIMED, Marseille). *, $p<0.05$; , $0.001<p<0.01$; * $p<0.001$; Student's t-test.

Figure 4:
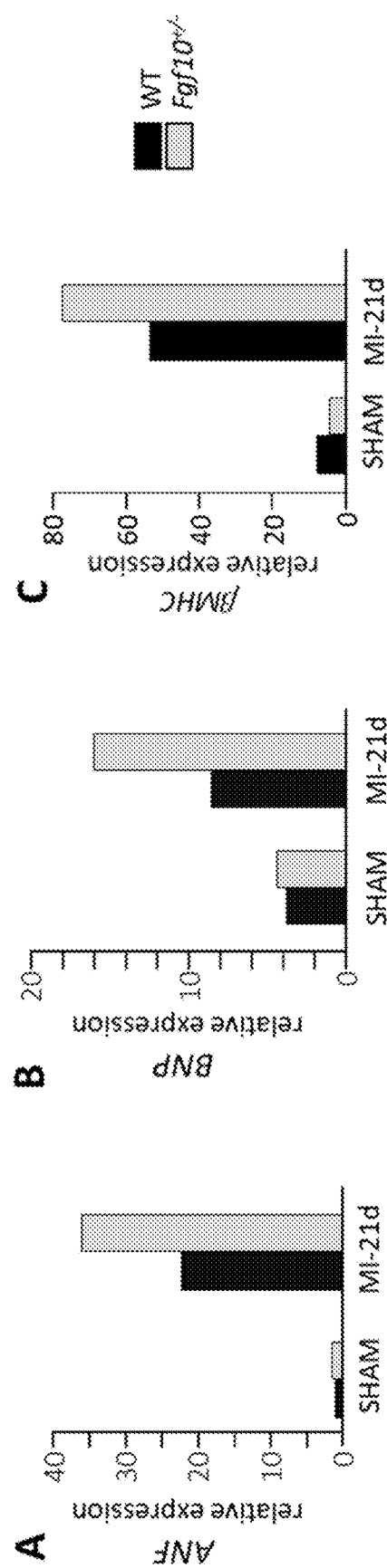

FIG. 4: Decreased Fgf10 dosage worsens pathological heart remodeling after myocardial infarction. WT and Fgf10$^{+/-}$ adult mice were subjected to myocardial infarction. qRT-PCR experiments were performed on left ventricular tissues three weeks after myocardial infarction (MI-21 d). A-C depict key heart failure markers using qRT-PCR experiments in Fgf10$^{+/-}$ infarcted mice compared to WT infarcted mice.

Figure 5:
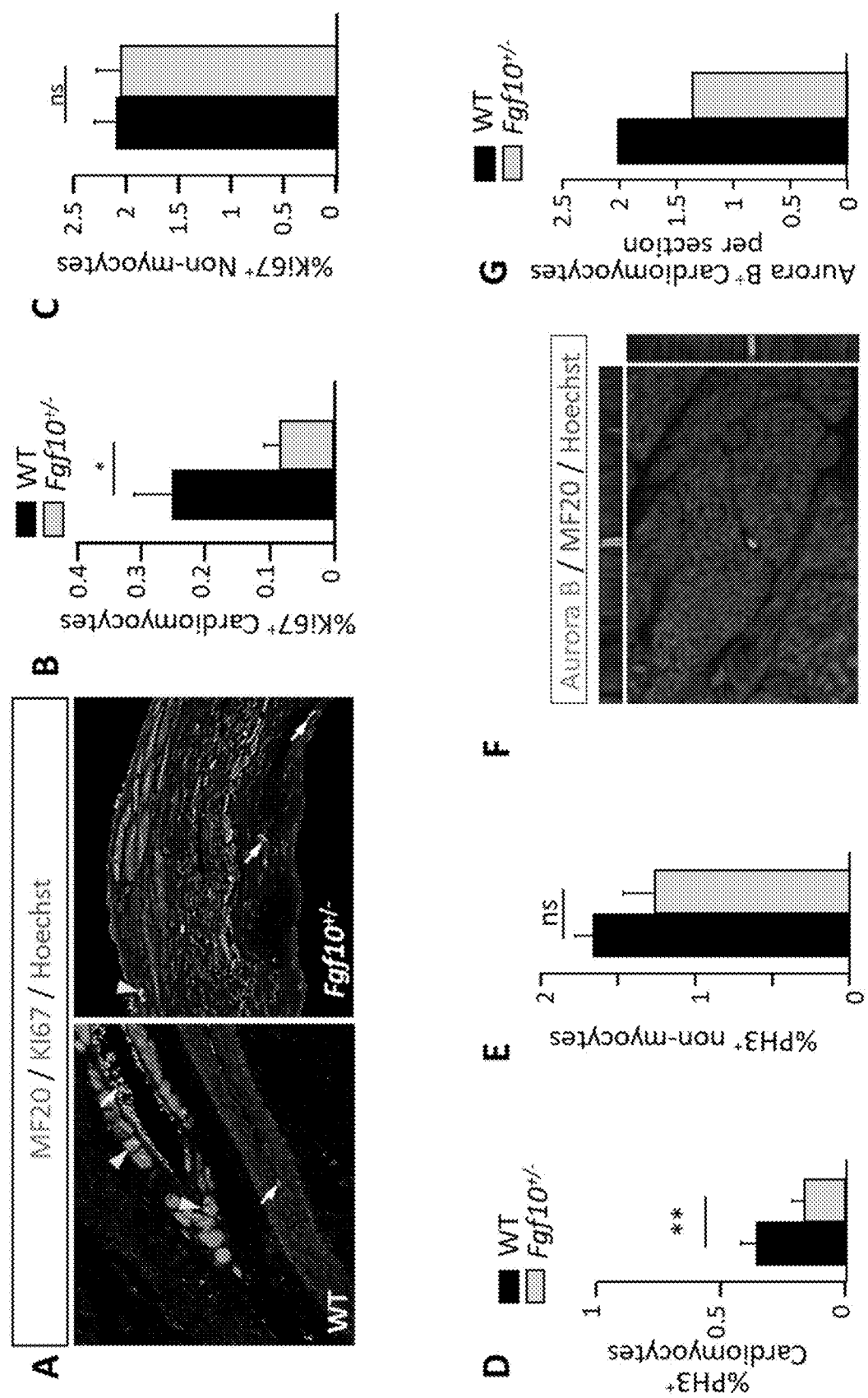

FIG. 5: Decreased Fgf10 dosage significantly impairs maximal cardiomyocyte proliferation capacities. WT and Fgf10+/− adult mice were subjected to myocardial infarction. (A) Three weeks post-MI, immunofluorescence experiments on paraffin sections were performed to evaluate cardiomyocyte (MF20+; yellow arrowheads) and non-cardiomyocyte (MF20−; white arrows) proliferation (Ki67+). (B) Significant impairment of cardiomyocyte proliferation levels in Fgf10+/−-MI mice compare to WT-MI mice was observed. (C) No alteration in non-myocyte proliferation was detected. (D-G) Proliferation was evaluated 5 days post-MI. (D) Immunofluorescence using PH3 antibody revealed significant impairment of cardiomyocyte proliferation levels in Fgf10+/−-MI mice compare to WT-MI mice. (E) No alteration in non-myocyte proliferation was detected. (F) Immunofluorescence using the cytokinesis marker Aurora B confirmed cardiomyocyte cell division impairment in Fgf10+/−-MI mice compare to WT-MI mice (G). ns, non-significant; *, $p<0.05$; **, $0.001<p<0.01$; Student's t-test.

Figure 6:
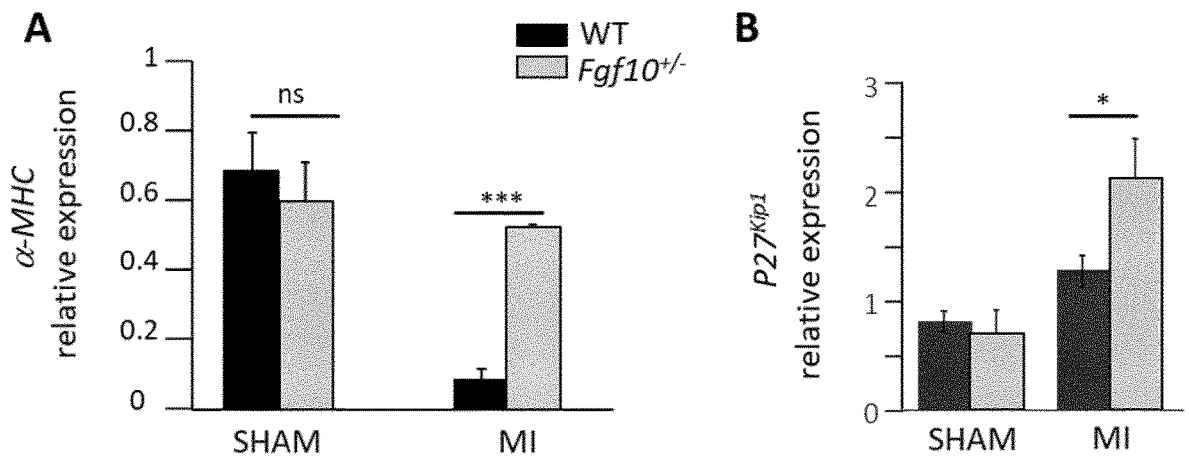

FIG. 6: Decreased Fgf10 dosage impairs maximal cardiomyocyte proliferation capacities though upregulated $p27^{kip1}$ and αMHC expression levels. WT and Fgf10+/− adult mice were subjected to myocardial infarction. qRT-PCR experiments were performed on left ventricular tissues 5 days (A) and three weeks after myocardial infarction (B). ns, non-significant; ***, $p<0.001$; Student's t-test.

Figure 7:
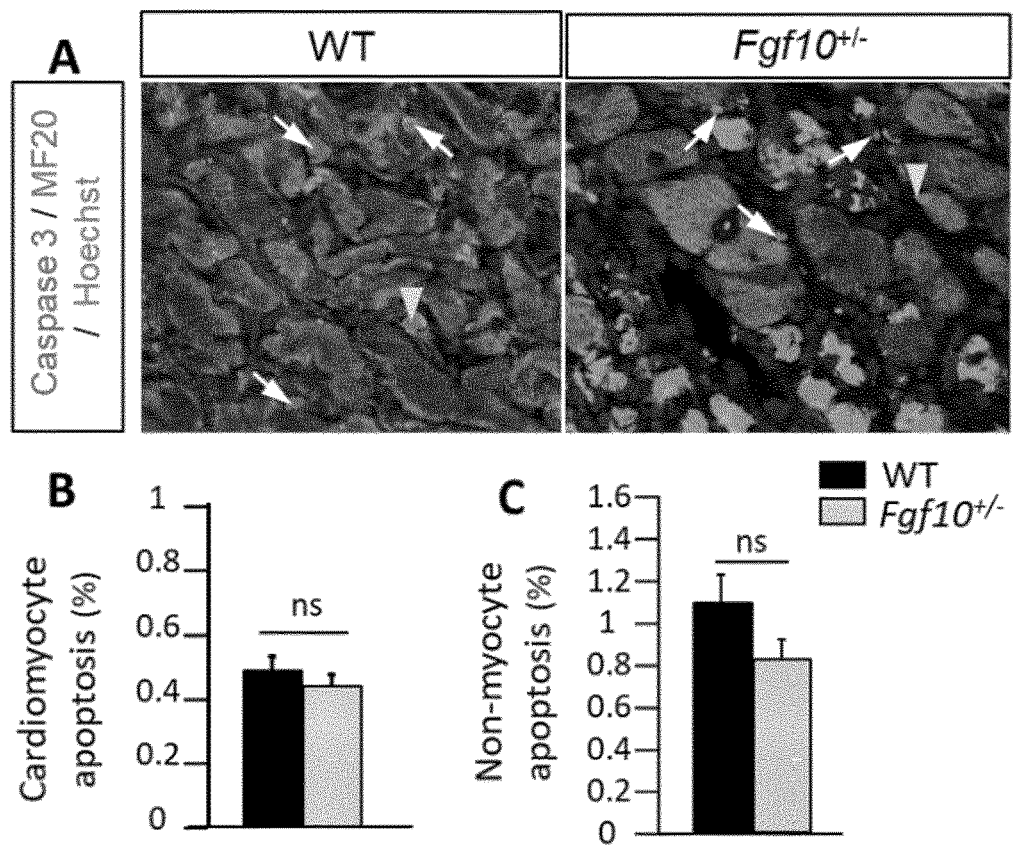

FIG. 7: Decreased Fgf10 dosage has no impact on cell survival after MI. WT and Fgf10+/− adult mice were subjected to myocardial infarction. (A) Five days post-MI, immunofluorescence experiments on paraffin sections were performed to evaluate cardiomyocyte (MF20+; yellow arrowheads) and non-cardiomyocyte (MF20−; white arrows) apoptosis (Caspase3+). (B-C) No apoptosis alteration was detected. ns, non-significant; Student's t-test.

Figure 8:
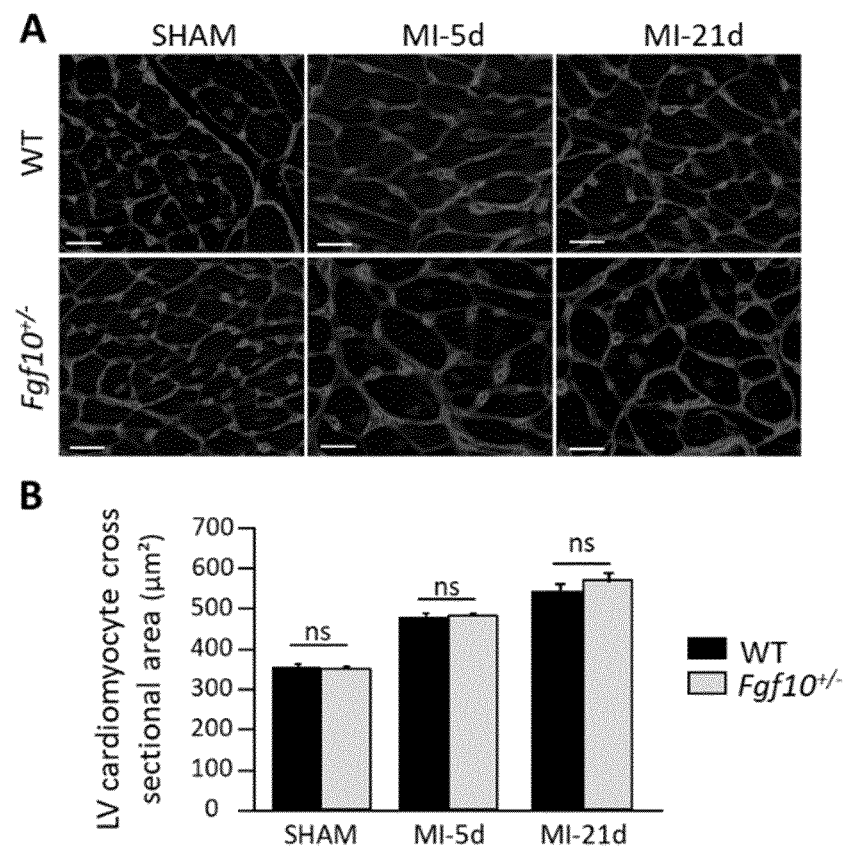

FIG. 8: Decreased Fgf10 dosage has no impact on cardiomyocyte hypertrophy. WT and Fgf10+/− adult mice were subjected to myocardial infarction. (A) Five days (MI-5 d) and three weeks (MI-21 d) post-MI, immunofluorescence experiments on paraffin sections were performed to evaluate cardiomyocyte cross-sectional area (WGA-TRITC). (B) No difference in cardiomyocyte size was detected. ns, non-significant; Student's t-test.

Figure 9:
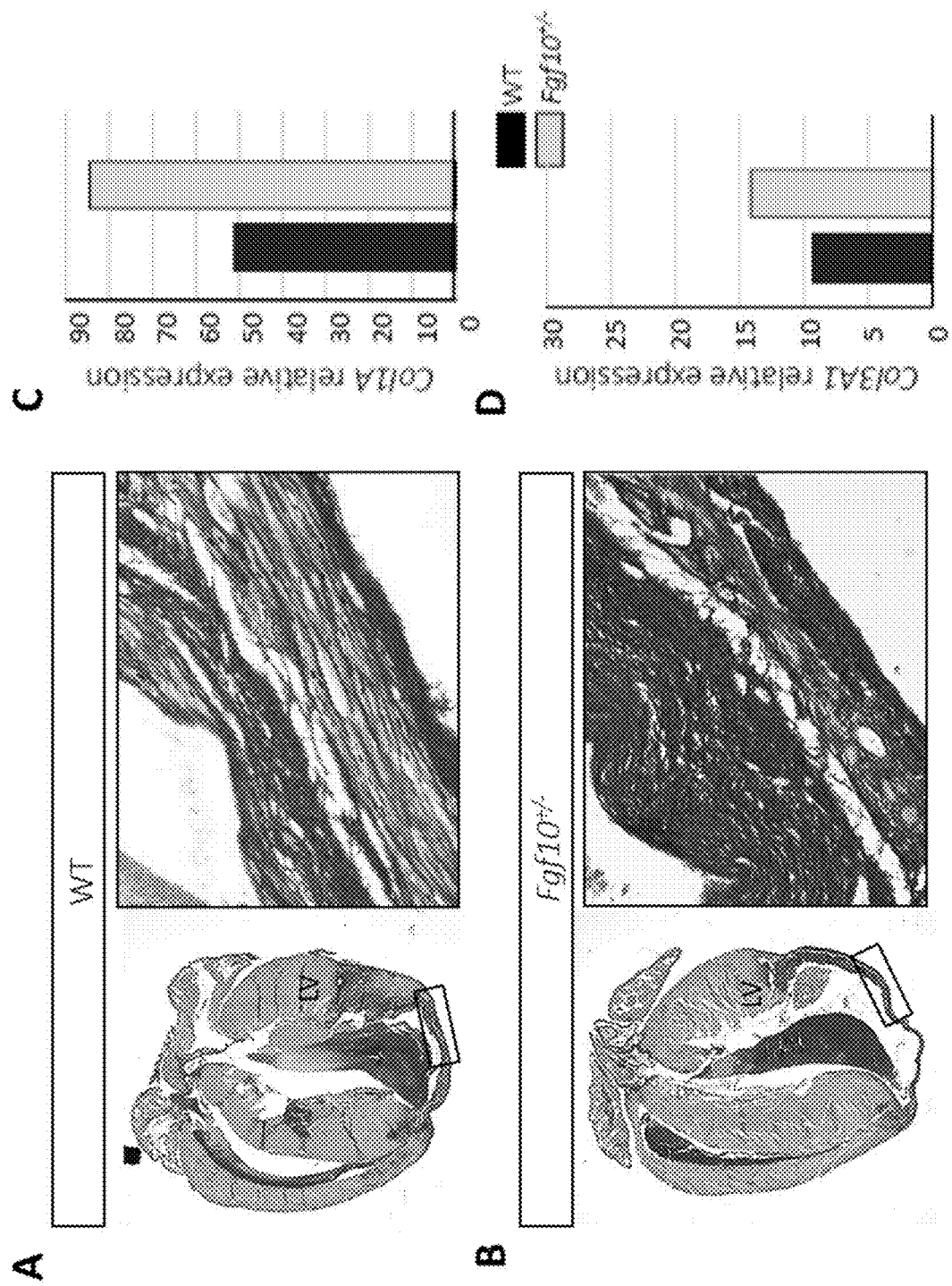

FIG. 9: Decreased Fgf10 dosage worsens fibrosis infiltration 3 weeks post-MI. WT and Fgf10+/− adult mice were subjected to myocardial infarction. 21 days post-MI, histological sirius red staining performed on paraffin sections revealed that compare to WT-MI mice (A), Fgf10+/−-MI (B) mice displayed further fibrosis deposition. qRT-PCR experiments performed on left ventricular tissues 21 days after myocardial infarction showed upregulated levels of Col1A (C) and Col3A1 (D) genes in Fgf10+/−-MI compare to WT-MI mice.

Figure 10:
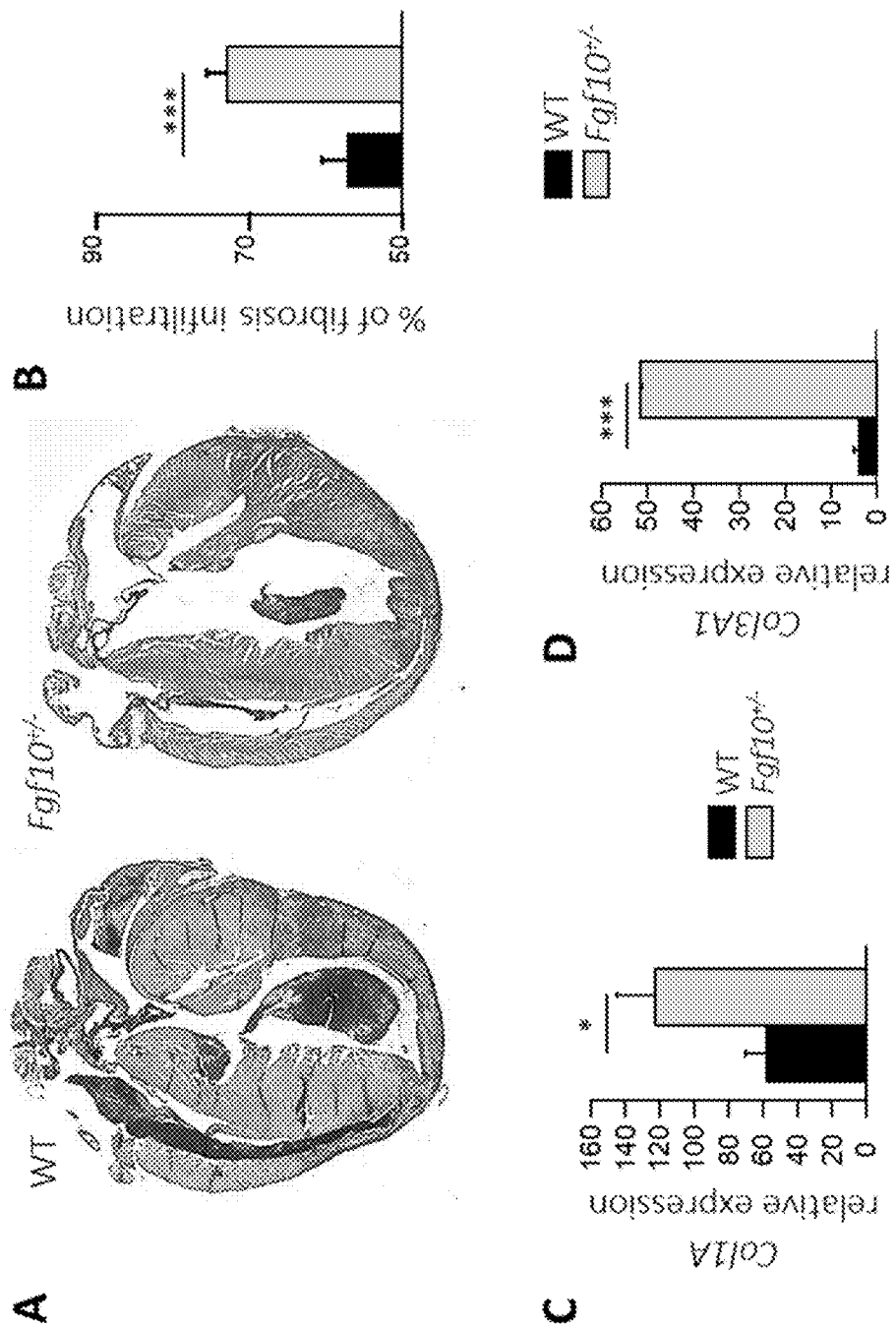

FIG. 10: Decreased Fgf10 dosage worsens fibrosis infiltration 5 days post-MI. WT and Fgf10+/− adult mice were subjected to myocardial infarction. (A) Five days post-MI, histological experiments on paraffin sections were performed to evaluate fibrosis infiltration (Sirius-red staining). (B) Bioinformatic quantification revealed that Fgf10+/−-MI mice displayed further fibrosis deposition compare to WT-MI mice. qRT-PCR experiments performed on left ventricular tissues showed upregulated levels of Col1A (C) and Co3A1 (D) in Fgf10+/−-MI compare to WT-MI mice. *, $p<0.05$; ***, $p<0.001$; Student's t-test.

Figure 11:
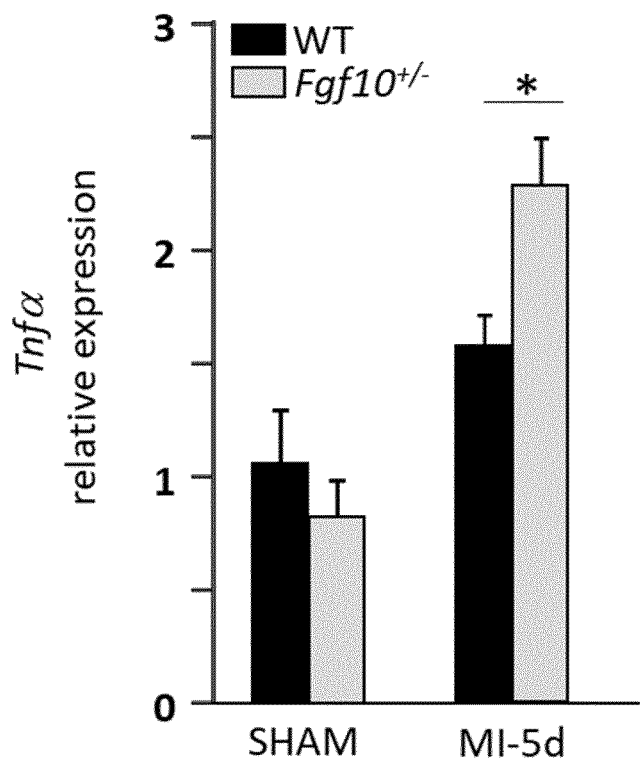

FIG. 11: Decreased Fgf10 dosage worsens inflammatory response following myocardial infarction. WT and Fgf10+/− adult mice were subjected to myocardial infarction. 5 days post-MI, qRT-PCR experiments performed on left ventricular tissues revealed upregulated Tnfα levels in Fgf10+/−-MI mice compare to WT-MI mice. *, $p<0.05$; Student's t-test.

Figure 12:

FIG. 12: Upregulation of Fgf10 levels post-MI preserves cardiac function. R26R-RTTA Tet(O)-Fgf10 mice were subjected to myocardial infarction. One day after MI, mice were fed with normal or doxycycline supplemented food required to induce Fgf10 overexpression. Echocardiographic experiments performed 21 days post-MI revealed that Fgf10 upregulation preserves cardiac function post-MI.

Figure 13:
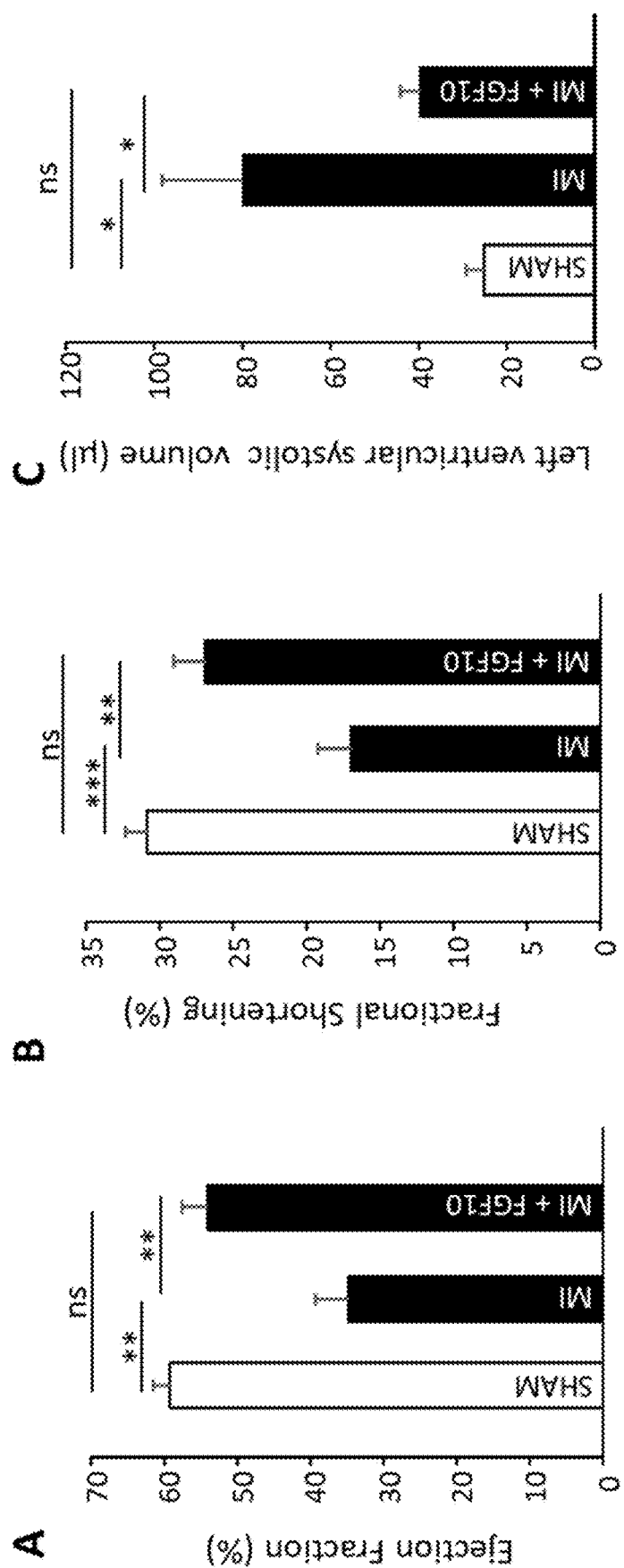

FIG. 13: Upregulation of Fgf10 levels post-MI preserves cardiac function and remodeling. R26R-RTTA Tet(O)-Fgf10 mice were subjected to myocardial infarction. One day after MI, mice were fed with normal or doxycycline supplemented food required to induce Fgf10 overexpression. Echocardiographic experiments performed 21 days post-MI revealed that Fgf0 upregulation preserves ejection fraction (A), fractional shortening (B) and left ventricular systolic volume (C) post-MI. ns, non-significant; *, $p<0.05$; , $0.001<p<0.01$; *, $p<0.001$; Student's t-test.

Figure 14:
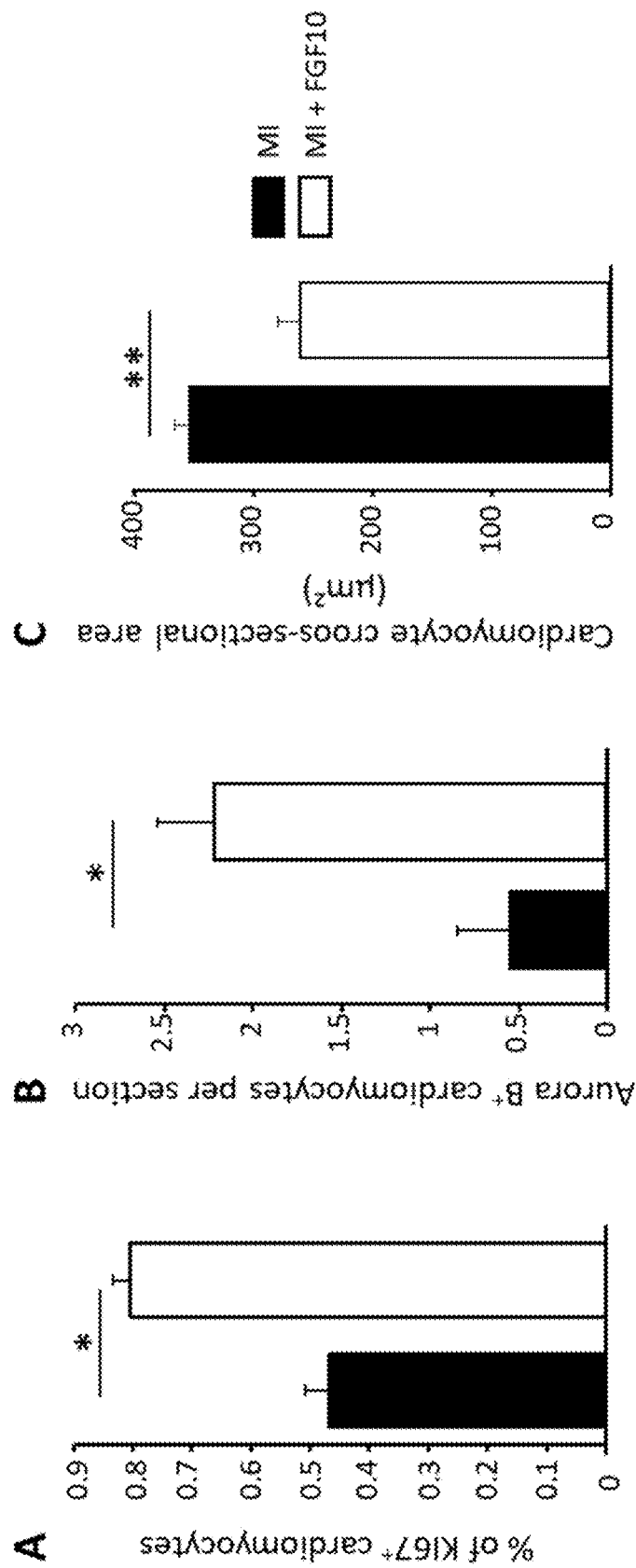

FIG. 14: Upregulation of Fgf10 levels post-MI promotes cardiomyocyte proliferation. R26R-RTTA Tet(O)-Fgf10 mice were subjected to myocardial infarction. One day after MI, mice were fed with normal (CTRL) or doxycycline (DOX) supplemented food required to induce Fgf0 overexpression. Three weeks post-MI, immunofluorescence experiments on paraffin sections were performed to evaluate cardiomyocyte (MF20+) proliferation (Ki67+ and AuroraB+). Significant increase in cardiomyocyte proliferation (A) and cardiomyocyte cytokinesis (B) were observed in levels in R26R-RTTA Tet(O)-Fgf10-MI mice treated with DOX food compare to R26R-RTTA Tet(O)-Fgf10-MI mice treated with CTRL food. (C) Immunofluorescence experiments on paraffin sections performed to evaluate cardiomyocyte cross-sectional area (WGA-TRITC) revealed decreased cardiomyocytes size in R26R-RTTA Tet(O)-Fgf10-MI mice treated with DOX food compare to R26R-RTTA Tet(O)-Fgf10-MI mice treated with CTRL food. *, $p<0.05$; **, $0.001<p<0.01$; Student's t-test.

Figure 15:
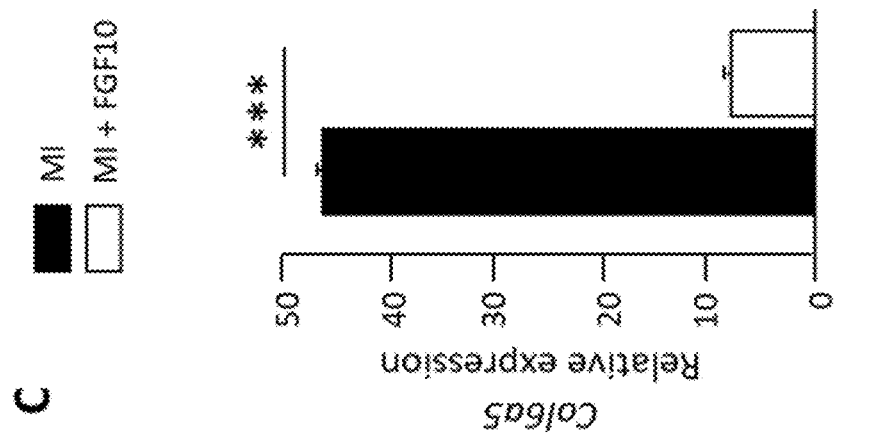
Figure 15:
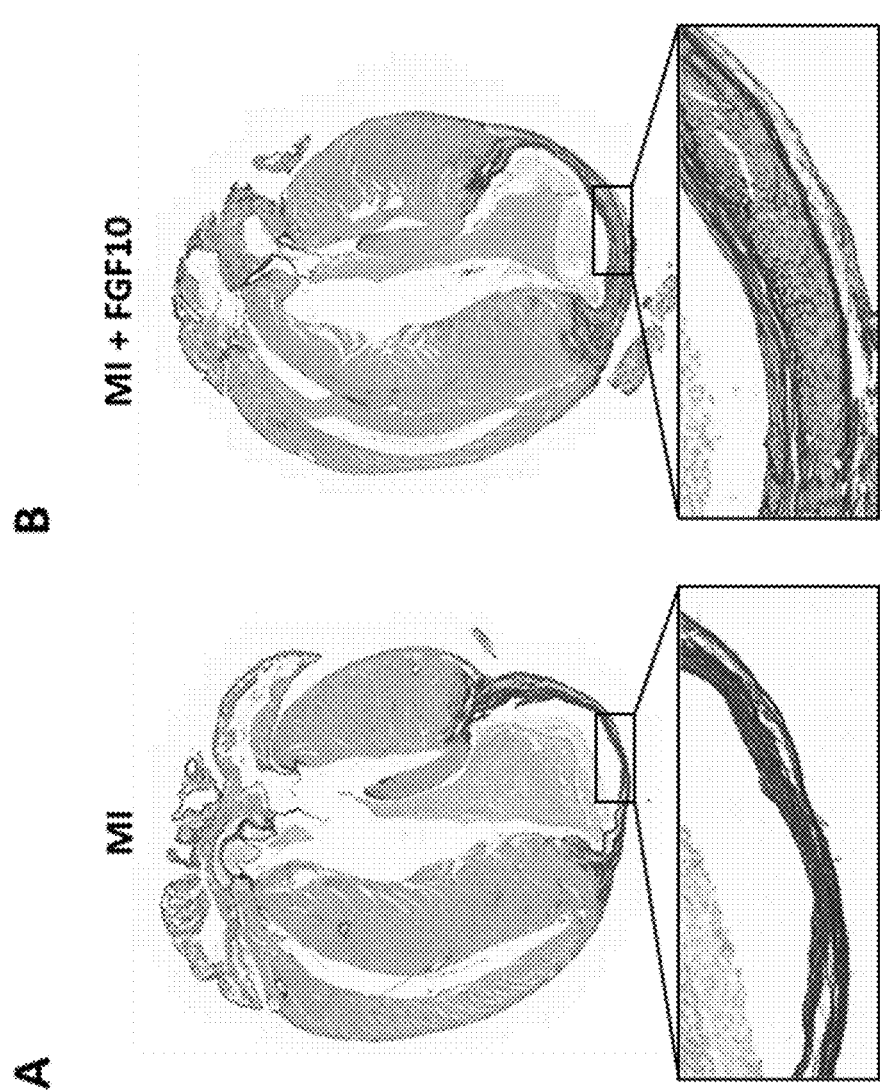

FIG. 15: Upregulation of Fgf10 levels post-MI prevents fibrosis infiltration 3 weeks post-MI. R26R-RTTA Tet(O)-Fgf10 mice were subjected to myocardial infarction. One day after MI, mice were fed with normal (CTRL) or doxycycline (DOX) supplemented food required to induce Fgf0 overexpression. 21 days post-MI, histological sirius red staining performed on paraffin sections revealed that compare R26R-RTTA Tet(O)-Fgf10-MI mice treated with CTRL food (A), R26R-RTTA Tet(O)-Fgf10-MI mice treated with DOX food (B) mice displayed reduced fibrosis deposition. (C) qRT-PCR experiments performed on left ventricular tissues 21 days after myocardial infarction showed downregulated levels of Col6A5 gene in R26R-RTTA Tet(O)-Fgf10-MI mice treated with DOX food compare to R26R-RTTA Tet(O)-Fgf10-MI mice treated with CTRL food.

Figure 16:
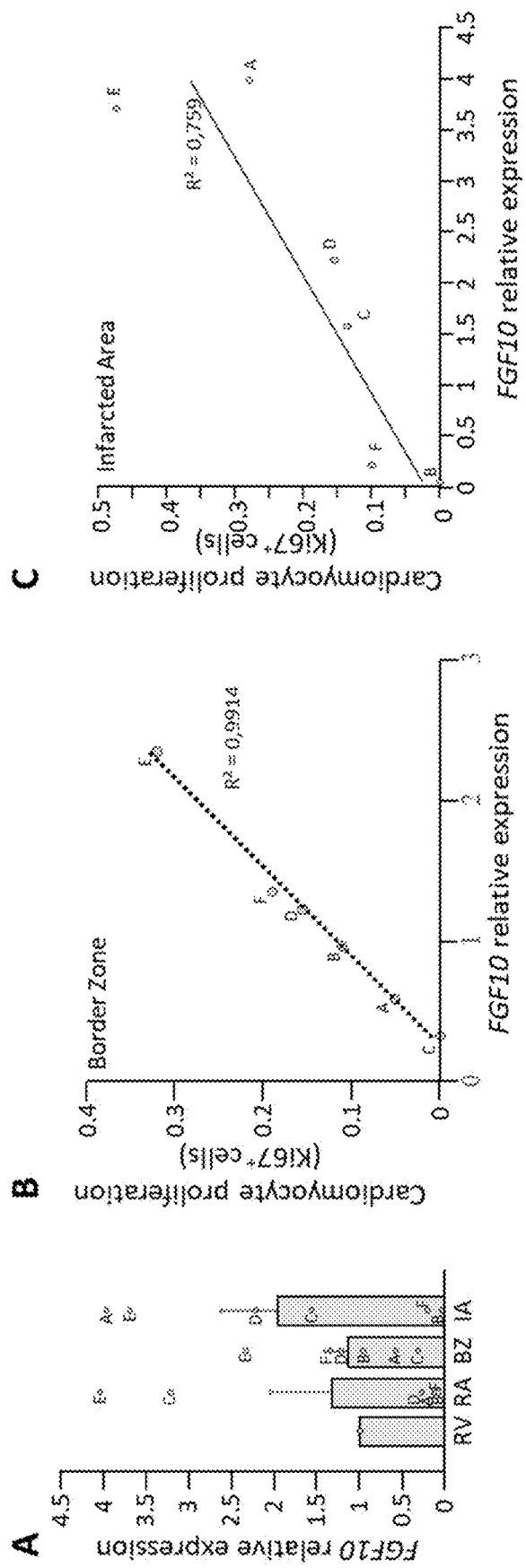

FIG. 16: FGF10 upregulated levels in human failing heart correlate with increased cardiomyocyte proliferation. Human explanted failing heart samples from right ventricle (RV), remote area (RA), border zone (BZ) and infarcted area (IA) were collected from 6 patients (A-F). (A) qRT-PCR experiments revealed upregulated FGF10 levels in the BZ (3 patients out of 6) and the IA (4 patients out of 6). Immunofluorescence experiments using the cell cycle marker Ki67 showed that elevated FGF10 levels correlate with enhanced cardiomyocyte proliferation in the BZ (B) and the IA (C).

Figure 17:
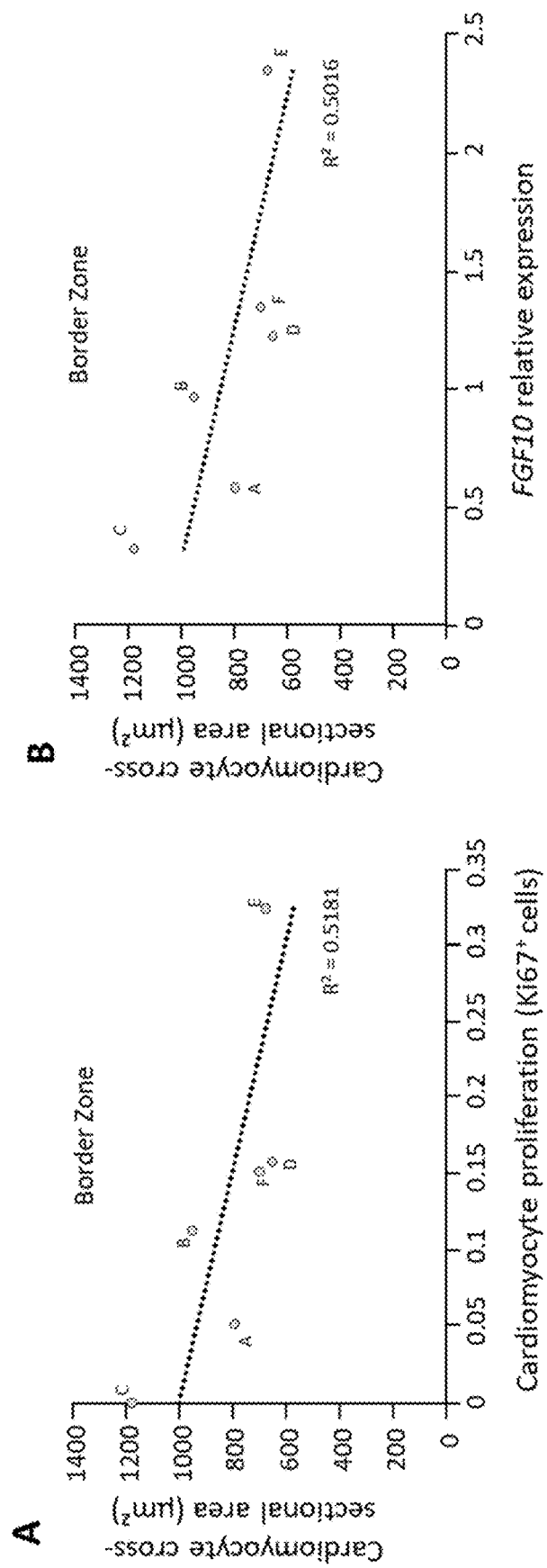

FIG. 17: FGF10 upregulated levels in human failing heart correlate with reduced cardiomyocyte size. Human explanted failing heart samples were collected from 6 patients (A-F). Immunofluorescence experiments using the cell membrane marker WGA showed that reduced cardiomyocyte cell size correlate in the border zone with (A) increased cardiomyocyte proliferation and (B) elevated FGF10 levels correlate.

Figure 18:
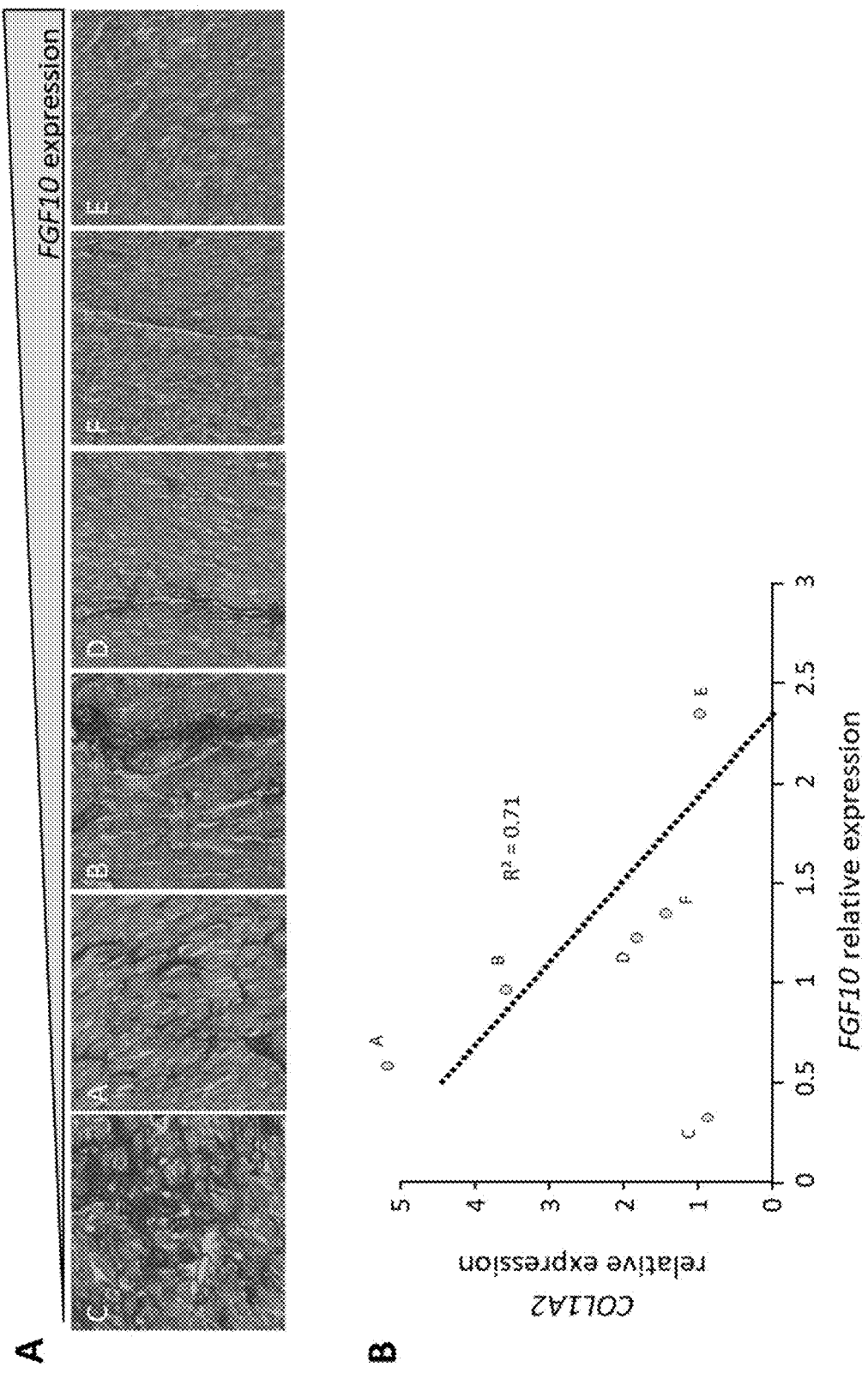

FIG. 18: FGF10 upregulated levels in human failing heart correlates with reduced fibrosis infiltration. Human explanted failing heart samples were collected from 6 patients (A-F). Histological sirius red staining (A) and qRT-PCR experiments (B) showed that elevated FGF10 levels correlate with reduced fibrosis infiltration in the border zone.

DETAILED DESCRIPTION OF THE INVENTION

The present invention provides a novel strategy for the treatment of a heart disease. It is based on the unexpected finding that FGF10 is able to promote cell cycle re-entry of cardiomyocytes in mouse heart.

Fibroblast Growth Factor 10 (FGF10) is a protein that plays an important role in the regulation of embryonic development, cell proliferation and cell differentiation. Notably, it is required for normal branching morphogenesis. According to the invention, FGF10 may be derived from any species. However, in a preferred embodiment, in particular for human therapy, FGF10 is derived from primates such as non-human primates or is human FGF10. In a particular embodiment, FGF10 is human FGF10 (such as FGF10 with Uniprot accession number O15520).

According to an aspect, the present invention relates to FGF10 or a vector encoding FGF10, or an activator of FGF10 signaling pathway, for use as a medicament.

The invention relies on the delivery of FGF10 or of an activator of FGF10 signaling pathway to the cardiac tissue of a subject in need thereof.

A subject in need of FGF10 or of an activator of FGF10 signaling pathway is a mammal subject, such as a human subject, having or at risking of having a heart disease. The subject is suffering from heart disease such as myocardial infarction or ischemic heart disease (e.g. chronic ischemic heart disease).

In the context of the present invention, the term "therapeutic agent" denotes the FGF10 protein or the vector encoding the same, or the activator of FGF10 signaling pathway, or a cell encoding and secreting FGF10 or an activator of FGF10 signaling pathway, all being molecules or complexes, or cells that may be used in the present invention.

According to the present invention, the expression "activator of FGF10 signaling pathway" means a compound (e.g. a small molecule, a protein, a nucleic acid or a vector) that may activate FGF10 expression or FGF10 signaling. For example, the activator may be an agonist of the FGF10 receptor. Alternatively, the activator may act on a pathway that is downstream of the FGF10 receptor, or to an unrelated pathway, as long as the activator action results in an activation of the FGF10 signaling pathway.

In a particular embodiment of the invention, the therapeutic agent is FGF10 or a vector encoding FGF10.

Delivery may be achieved according to a number of means, such as by administering a recombinant protein or an expression vector.

In a particular embodiment, delivery is achieved by administering a recombinant protein such as a FGF10 protein or an activator of the FGF10 signaling pathway that is a protein. In a particular embodiment, the recombinant protein is FGF10 protein.

In another particular embodiment, delivery is achieved by administering an expression vector, such as a vector encoding FGF10 or a vector encoding an activator of the FGF10 signaling pathway. In a particular embodiment, the expression vector encodes FGF10.

According to the present invention, an "expression vector" is a vector, such as a plasmid or a viral vector, comprising a nucleic acid sequence encoding an agent useful for therapy in the context of the present invention, operably linked to a promoter. An "expression vector encoding FGF10" comprises a nucleic acid sequence encoding FGF10, operably linked to a promoter. Relying on vectors, such as on viral vector, has the advantage of resulting in the constitutive expression of the encoded agent, such as FGF10, from a cell or tissue of interest, in particular from cardiac cells.

In a particular embodiment, the promoter is a promoter functional in cardiac cells, such as an ubiquitous promoter (for example the CMV promoter) or a cardiac-specific promoter (such as the αMHC and TnT promoters).

Viral vectors useful in the practice of the invention include, without limitation, adenoviral vectors, retroviral vectors, lentiviral vectors and AAV vectors. In a particular embodiment, the viral vector is an AAV vector. In a more particular embodiment, the AAV vector is selected from the group consisting of an AAV1, AAV6, AAV8, AAV9 and AAVM41 vector.

Furthermore, a cell for use according to the present invention may be a cardiac cell, or a stem cell that has been induced into the cardiomyocyte lineage, such as an induced pluripotent stem (iPS) or an embryonic stem (ES) cell that was induced into the cardiomyocyte lineage. The cell is further modified by introducing therein an expression cassette of FGF10, or an expression cassette of an activator of the FGF10 signaling pathway.

Delivery of the therapeutic may be done through a number of routes, for example via the oral, intramuscular, subcutaneous or intraperitoneal route, or preferably intravascularly (such as intra-arterially or intravenously) or through injection into the heart of the subject, such as by intracardiac or intracoronary injection.

The therapeutic for use according to the present invention may be in the form of an injectable composition comprising a therapeutically effective amount of the therapeutic, and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

In a preferred embodiment, the composition is formulated in accordance with routine procedures as a pharmaceutical composition adapted for intravascular administration, such for intravenous or intra-arterial administration, to human beings. Typically, compositions for intravascular administration are solutions in sterile isotonic aqueous buffer. Where necessary, the composition may also include a solubilizing agent and a local anesthetic such as lidocaine to ease pain at the site of injection.

The therapeutic is used in a therapeutically effective amount. The amount of the therapeutic which will be effective in the treatment of a heart disease can be determined by standard clinical techniques. In addition, in vivo and/or in vitro assays may optionally be employed to help predict optimal dosage amounts. The precise amount to be employed will also depend on the route of administration, and the seriousness of the disease, and should be decided according to the judgment of the practitioner and each patient's circumstances. The amount of the therapeutic administered to the subject in need thereof will vary based on several factors including, without limitation, the route of administration, the specific disease treated, the subject's age or the level of protein required, or the level of expression necessary to achieve the therapeutic effect. One skilled in the art can readily determine, based on its knowledge in this field, the dosage range required based on these factors and others.

The term "treatment" is used herein to refer to any regimen that can benefit an animal, in particular a mammal, more particularly a human subject. Accordingly, a treatment may include curative, alleviation or prophylactic effects. Accordingly, therapeutic and prophylactic treatment include amelioration of the symptoms of a particular heart disease or preventing or otherwise reducing the risk of developing a particular heart disease. The term "prophylactic" may be considered as reducing the severity or the onset of a particular condition. "Prophylactic" also includes preventing reoccurrence of a particular condition in a patient previously diagnosed with the condition. "Therapeutic" may also include the reduction of the severity of an existing condition.

The therapeutic agent of the invention may be used in the treatment of a heart disease. Particular heart diseases that may be treated according to the invention include, without limitation, infarction or ischemic heart disease (e.g. chronic ischemic heart disease). In addition, the invention may be implemented to treat heart fibrosis or heart inflammation. In addition, the invention may be implemented for the prevention of congestive heart failure. In another aspect, the therapeutic agent is for use in the treatment of any consequence of a heart disease. Particular consequences of a heart disease include, without limitation, heart fibrosis and heart inflammation.

In addition, the therapeutic agent may be used to improve angiogenesis and revascularization into the heart.

The administration of the therapeutic agent is preferably done the earliest after onset of the heart disease. In particular, the administration may be done the same day as the day of infarction, or the day the patient is medically taken care for a heart disease or is diagnosed with a heart disease. In a particular embodiment, administration may be done up to normalization of cardiac physiological parameters, although administration may be conducted for a longer time. In a particular embodiment, the therapeutic agent is administered the earliest after onset of the heart disease, and up to normalization of cardiac physiological parameters.

The administration of the therapeutic agent, in particular of FGF10 protein or a vector encoding the same, may include single or multiple administrations. In particular, administration may be done, for example, once a day, once a week or once a month during a time sufficient for the treatment of the disease to be effective. In a particular embodiment, where the disease is myocardial infarction, the therapeutic agent, for example a protein (such as FGF10), is administered a short time after the day of infarction. In particular, administration may be done the same day as myocardial infarction, or one day after the episode of myocardial infarction, or may be done the same day as the patient in need thereof is medically taken care of for a heart disease or is diagnosed with a heart disease, or the day after medical care or diagnosis. In a further particular embodiment, therapeutic agent administration (such as administration of a protein, for example FGF10 administration) is done daily starting from the day of infarction (otherwise referred to as day 0) or from the day of medical care or diagnosis of the patient. In another embodiment, therapeutic agent administration (such as administration of a protein, for example FGF10 administration) is done daily starting from the day after the day of infarction (i.e. at day 1) or from the day after medical care or diagnosis of the patient, or starting from 2 days (i.e. at day 2) after the day of infarction or after the day of medical care or diagnosis of the patient. In a variant of this embodiment, therapeutic administration (such as administration of a protein, for example FGF10 administration) is done daily starting from day 0, from day 1 or from day 2 after myocardial infarction or from the day of medical care or diagnosis of the patient. In a particular embodiment, the administration is discontinuous, i.e. administration is not done daily. In a further particular embodiment, the administration is done daily during the treatment phase. In another embodiment, the treatment is an acute treatment, done for a short period of time (such as for several days, for example for no more than 30 days, 29, 28, 27, 26, 25, 24, 23, 21, 20, 19, 18, 17, 16, 15, 14, 13, 12, 11 or no more than 10 days). In another particular embodiment, the treatment is a chronic treatment, wherein administration of the therapeutic agent is done for at least several weeks, several months, or even several years.

In another aspect, the invention relates to a method for preparing a heart transplant, comprising immersing a heart which will undergo a transplant into a medium containing FGF10 or an activator of the FGF10 signaling pathway. Thanks to the method of the invention, the heart to be transplanted is preserved and activated thanks to the medium it is immersed into. The medium may further comprise one or more components such as salts (for example NaCl or KCl), and other growth factors.

The invention will now be described with reference to the following examples.

EXAMPLES

Example 1

Material and Methods

Transgenic mouse lines and genotyping. Fgf10+/−, Fgf10-LacZ, Rosa26-rtTA and Tet(O)-Fgf10 mice were maintained on mixed C57Bl/6, CD1 and inbred FVB/N backgrounds, respectively. Inducible expression of Fgf0 is achieved by feeding sequentially mice with food containing doxycycline (625 mg/kg DOX, Envigo). Cervical dislocation method was used for mice sacrifice. Animal care was in accordance with national and institutional guidelines. Mice were genotyped using DNA extracted from adult tail tips. Samples were lysed in lysis buffer (50 mM KCL, 10 mM Tris, 2 mM MgCl2, 0.1 mg/ml gelatin, 0.45% of NP40 10%, 0.45% tween 20) with 1% Proteinase K (Roche, 11733400) for 2 hours at 55° C. to extract DNA and then followed by Proteinase K heat inactivation at 95° C. for 15 minutes.

PCR was performed using specific primers listed below. The PCR steps include pre-denaturation at 94° C. for 5 minutes, 30 cycles of denaturation (94° C. for 45 seconds), annealing (60° C. for 45 seconds) and extension (72° C. for 45 seconds) followed by a final extension step at 72° C. for 7 minutes. PCR products were separated using agarose gel electrophoresis to detect the specific amplified fragments.

Primers for Genotyping (Sequence 5'-3'):

```
Fgf10+/−-F1
                                      (SEQ ID NO: 1)
CTTCCAGTATGTTCCTTCTGATGAGAC;

Fgf10+/−-F2
                                      (SEQ ID NO: 2)
TACGGACAGTCTTCTTCTTGGTCCC;

Fgf10+/−-R
                                      (SEQ ID NO: 3)
GAGCTTGCTGGGGGAAACTTCCTGACTAGG;

Fgf10-LacZ-F
                                      (SEQ ID NO: 4)
ATCCTCTGCATGGTCAGGTC;

Fgf10-LacZ-R
                                      (SEQ ID NO: 5)
CGTGGCCTGATTCATTCC.
```

Rosa26-rtTA Mice:

```
For
                                      (SEQ ID NO: 6)
AAGTCGCTCTGAGTTGTTATCAG;

WT-Rev
                                      (SEQ ID NO: 7)
GGAGCGGGAGAAATGGATATGA;

Mut-Rev
                                      (SEQ ID NO: 8)
CGGGTTGTTAAACCTTCGATTCCG.
```

Tet(O)-Fgf10 Mice:

```
For
                                      (SEQ ID NO: 9)
GACGCCATCCACGCTGT;

Rev
                                      (SEQ ID NO: 10)
TGCTGCCAGTTAAAAGATGC.
```

Myocardial infarction model. Adult mice were sedated with isoflurane and, following endotracheal intubation, were artificially ventilated. Following skin incision, lateral thoracotomy at the fourth intercostal space was performed by blunt dissection of the intercostal muscles. Following left anterior descending coronary artery ligation (with 8.0 non-absorbable silk sutures), thoracic wall and skin incisions were sutured with 6.0 non-absorbable and 4.0 absorbable silk sutures, respectively. Mice were then warmed for several minutes until recovery.

Echocardiography. Heart function was evaluated at the CERIMED-Marseille, by transthoracic echocardiography performed on isoflurane-sedated mice using a Vevo 2100 VisualSonics. All echocardiography measurements were performed in a blinded manner.

Tissue processing. Hearts were dissected and analyzed using a Zeiss Lumar stereo dissecting microscope. For X-gal staining, hearts were collected and fixed for 3 hours in 4% paraformaldehyde (PFA), extensively washed in 1×PBS and stained for 12 hours at 37° C. in a solution containing 4 mg/ml of X-gal. After staining, the samples were washed in PBS, post-fixed in PFA 4% and observed under a Zeiss Lumar stereomicroscope.

For immunostaining and sirius red staining, hearts were fixed in 4% PFA for 3 hours and extensively washed in 1×PBS. Paraffin embedding was performed following dehydration using a graded ethanol series (50, 70, 90 and 100%), two xylene washes and three paraffin washes (Paraplast X-tra, Sigma P3808). Cryopreservation was achieved by incubation of hearts in a sucrose series (15 and 30%) and embedding in OCT (VWR, 361603E).

Sirius red staining on paraffin sections. Serial 13 μm sections were obtained and mounted on poly-lysine-treated slides. After dewaxing (xylene, 2 times) and rehydration in an ethanol series (100, 90, 70, 50% and H2O), paraffin sections were incubated in a 0.1% Sirius Red solution dissolved in saturated aqueous solution of picric acid for 1 hour at room temperature. Subsequently, sections were washed 3 times in acidified water (0.5% acetic acid), dehydrated in ascending concentrations of ethanol (70%, 90% and 100%) and cleared in xylene. Sections were mounted in resinous medium (Entellan). Collagen and non-collagen components were red- and orange-stained, respectively.

Immunofluorescence on paraffin sections. Serial 13 μm sections were obtained and mounted on poly-lysine-treated slides. After dewaxing (xylene, 2 times) and rehydration in an ethanol series (100, 90, 70, 50% and H$_2$O), antigen was retrieved by boiling samples in Vector Antigen Unmasking Solution (Vector Laboratories, H-3300) for 15 min. Slides were allowed to cool to room temperature for 20 min and washed in PBS. For blocking, samples were incubated for at least 1 hour in TNB (0.1M Tris-HCl, 0.15M NaCl, 0.5% (w/v) blocking reagent (PerkinElmer FP1020) prior to incubation with antibodies in TNB overnight at 4° C. This was followed by 3 times PBS-Tween 0.05% (PBST) washes. Slides were then incubated with secondary antibody diluted in TNB for 1 hour at room temperature, followed by 3 washes in PBST and nuclei were counterstained with Hoescht (1/1000) and mounted using FluoroMount (Southern Biotech). Sections were imaged using a Zeiss Axiolmager fluorescent microscope with an Apotome module.

Immunofluorescence on frozen sections. Serial 13 μm cryostat sections were obtained from OCT embedded hearts. Sections were kept at room temperature for 15 min to dry and then washed with PBS. Slides were incubated for at least one hour in blocking solution (3% BSA-0.05% Saponin) prior to incubation with primary antibodies in blocking solution overnight at 4° C. This was followed by 3 washes in PBST. Slides were then incubated with secondary antibody in blocking solution for 1 hour at room temperature, followed by 3 washes in PBST. Nuclei were counterstained with Hoescht (1/1000) and mounted with FluoroMount (Southern Biotech). Sections were imaged using a Zeiss AxioImager fluorescent microscope with an Apotome module.

Primary antibodies: name/species/dilution/references:
α-actinin/Mouse/1/500/Sigma A7811
AuroraB/Rabbit/1/400/Abcam ab2254
Caspase 3/Rabbit/1/100/Cell signalling 9665
β-galactosidase/Rabbit/1/500/MP Biomedicals 0855976
Ki-67/Rat/1/25/Dako M7249
MF20 sarcomeric myosin heavy chain/Mouse/1/50/DSHB
Phospho Histone H3/Rabbit/1/400/Upstate cell signalling 06-570
WGA-AlexaFluor555/1/50/Thermofisher W32464.

Secondary antibodies: name/species/dilution/references:
Anti-Rabbit Alexa Fluor 488/Donkey/1/500/ThermoFisher A-21206
Anti-Mouse Alexa Fluor 488/Donkey/1/500/ThermoFisher A-21202
Anti-Mouse Alexa Fluor 647/Donkey/1/500/ThermoFisher A-31571
Anti-Rat Alexa Fluor 488/Donkey/1/500/ThermoFisher A-21208
Anti-Rat Alexa Fluor 647/Goat/1/500/ThermoFisher A-21247.

Quantitative Real Time PCR. Total RNA was extracted using Trizol LS reagent (Life technologies). First strand cDNA was synthesized using Maxima Reverse Transcriptase (Life technologies). qRT-PCR was performed using the following primers and Luminaris qPCR SuperMix (Life technologies) and a Roche Light Cycler 480. Each experiment was performed in duplicate and normalized to Hprt. Quantitative RT-PCR primers are the following:

```
ANF-F
                                   (SEQ ID NO: 11)
CAACACAGATCTGATGGATTTCA,

ANF-R
                                   (SEQ ID NO: 12)
CCTCATCTTCTACCGGCATC,

BNP-F
                                   (SEQ ID NO: 13)
GTCAGTCGTTTGGGCTGTAAC,

BNP-R
                                   (SEQ ID NO: 14)
AGACCCAGGCAGAGTCAGAA,

Col1A-F
                                   (SEQ ID NO: 15)
CATGTTCAGCTTTGTGGACCT,

Col1A-R
                                   (SEQ ID NO: 16)
GCAGCTGACTTCAGGGATGT,

Col3A1-F
                                   (SEQ ID NO: 17)
TGGTCCTGCTGGAAAGGAT,

Col3A1-R
                                   (SEQ ID NO: 18)
GAGGTCCAGGCAGTCCAC,

Fgf10-F
                                   (SEQ ID NO: 19)
GAGAAGAACGGCAAGGTCAG,

Fgf10-R
                                   (SEQ ID NO: 20)
TTTCCCCTTCTTGTTCATGG,

Hprt-F
                                   (SEQ ID NO: 21)
CTGGTGAAAAGGACCTCTCG,

Hprt-R
                                   (SEQ ID NO: 22)
TGGCAACATCAACAGGACTC, p27kip1-F
                                   (SEQ ID NO: 23)
AACTAACCCGGGACTTGGAG, p27kip1-R
                                   (SEQ ID NO: 24)
AGTAGAACTCGGGCAAGCTG, aMHC-F
                                   (SEQ ID NO: 25)
CCTCAAGCTCATGGCTACAC, aMHC-R
                                   (SEQ ID NO: 26)
TTGCCTCCTTTGCCTTTACC, bMHC-F
                                   (SEQ ID NO: 27)
AGGCAAAGAAAGGCTCATCC, bMHC-R
                                   (SEQ ID NO: 28)
TGGAGCGCAAGTTTGTCATA, TNFa-F
                                   (SEQ ID NO: 29)
AGCCTCTTCTCATTCCTGCTT, TNFa-R
                                   (SEQ ID NO: 30)
ATGAGAGGGAGGCCATTTG.
```

Here the inventors show the protective role of FGF10 signaling pathway on cardiac remodeling and function in the context of myocardial infarction. Indeed, unexpectedly the inventors using a mouse model of myocardial infarction demonstrate for the first time that FGF10 specifically promotes cardiomyocyte proliferation after myocardial infarction, leading to cardiac regeneration. In addition they show that FGF10 is also required to prevent cardiac fibrosis infiltration and to repress prolonged inflammation both parameters strongly participating to the deleterious cardiac remodeling post-infarction. Finally they clearly demonstrate that FGF10 is essential to preserve cardiac performance following myocardial infarction. Thus altogether, the inventors ascertained that FGF10 is crucial for cardiac regeneration and repair in pathological conditions.

In order to determine the role of FGF10 under pathological conditions, three-month old WT and Fgf10-LacZ mice were subjected to myocardial infarction through ligation of the left anterior descending coronary artery. Three weeks after ligation, mice were sacrificed, hearts were removed and stained for X-gal, representative of Fgf0 expression (FIG. 1A). Hearts from sham-operated animal presented almost no X-gal[+] cells in the left ventricle. In contrast multiple X-gal[+] cells grouped in clusters were detected in myocardial infracted hearts, suggesting that Fgf10 expression is upregulated in pathological conditions (FIG. 1A). qRT-PCR experiments on left ventricular tissues from WT-MI mice confirmed the upregulated Fgf10 levels in the injured ventricle (FIG. 1B). Analysis of cryostat sections from Fgf10-LacZ-MI hearts demonstrated that X-gal positive cells are present in left ventricular cardiomyocytes (FIG. 1C). All these results suggest that, upon myocardial infarction, Fgf10 expression is upregulated in left ventricular cardiomyocytes.

To test whether fluctuation of Fgf0 signaling components correlates with regenerative capacities, the analysis of Fgf10 expression pattern during the postnatal regenerative window (P1-5) has been performed using qRT-PCR experiments (FIG. 2). The results show that Fgf0 expression decreases after birth, strongly correlating with the loss of regenerative capacities, thus identifying FGF10 as a potential crucial regulator of cardiac regeneration.

In order to evaluate the role of FGF10 under pathological conditions, transgenic mice with reduced Fgf0 expression (Fgf10$^{+/-}$) were subjected to myocardial infarction and three weeks after myocardial infarction, in vivo heart function was investigated using echocardiography (CERIMED, Marseille). Compare to WT infarcted mice, Fgf10$^{+/-}$ infarcted mice displayed worsened cardiac remodeling (FIG. 3A) and function including decreased ejection fraction (FIG. 3B), decreased fractional shortening (FIG. 3C) and increased left ventricular dilation (FIG. 3D).

In addition, the analysis of key heart failure markers using qRT-PCR experiments confirmed the worsened pathological remodeling in Fgf10$^{+/-}$ infarcted mice compare to WT infarcted mice (FIGS. 4A-C).

How FGF10 would be protective upon myocardial infarction was then investigated by analyzing cardiac cell proliferation in WT compare to Fgf10$^{+/-}$ adult mice, three weeks (FIG. 5A-C) and 5 days (FIG. 5D-G) post-MI. Immunofluorescence analysis of the proliferative capacities at early and late time points following MI, using the pan-cell cycle marker Ki-67, the mitotic marker PK3 and the cytokinesis marker Aurora B, revealed a significant impairment of cardiomyocyte proliferation in Fgf10$^{+/-}$ infarcted mice compare to WT-MI mice. (FIGS. 5B, 5D and 5G). No alteration in non-myocyte proliferation capacity has been detected (FIGS. 5C and 5E).

In order to uncover the molecular mechanism by which FGF10 is required in pathological conditions to maintain maximal cardiomyocyte proliferation, the expression levels of the differentiation marker αMHC and the cell cycle inhibitor p27$^{Kip1}$ were evaluated in WT- and Fgf10$^{+/-}$-MI heart. qRT-PCR revealed that decreased Fgf10 dosage maintains high αMHC expression levels post-MI (FIG. 6A). In addition, compare to WT-MI hearts, up-regulated levels of p27$^{Kip1}$ were detected in Fgf10$^{+/-}$-MI hearts (FIG. 6B). Altogether these results demonstrate that FGF10 in pathological conditions in required to promote cardiomyocytes partial dedifferentiation and to limit p27$^{Kip1}$ expression, two critical requirements for adult cardiomyocyte cell cycle progression.

The impact of decreased Fgf0 dosage after MI on cell mortality 5 days post-MI (FIG. 7) and on cardiomyocyte hypertrophy 5 days and 3 weeks post-MI (FIG. 8) was then evaluated. No alteration in cell mortality (FIGS. 7B and 7C) or cardiomyocyte size (FIG. 8B) could be detected.

Histological analysis using sirius red staining was then performed to determine the role of FGF10 in the progression of cardiac fibrosis following MI. Three weeks post-MI increased fibrosis infiltration was observed in FGF10$^{+/-}$-MI hearts compare to WT-MI hearts (FIGS. 9A and B) correlating with upregulated collagen gene expression (Col1A1; FIG. 9C and Col3A; FIG. 9D).

Histological analysis performed at 5 days post-MI and led to similar observations (FIG. 10), strongly confirming that FGF10 is crucial to prevent early and late cardiac fibrosis accumulation post myocardial infarction.

Finally the role of FGF10 on the inflammatory response following myocardial infarction was evaluated (FIG. 11). qRT-PCR experiments on WT- and Fgf10$^{+/-}$-MI hearts 5 days post myocardial infarction demonstrate that in pathological conditions, Fgf0 is required to repress Tnfα expression and thus limits excessive inflammatory response.

Altogether these results show that, by promoting cardiomyocyte proliferation and preventing fibrosis infiltration, FGF10 preserves cardiac performance post-myocardial infarction. Thus in order to determine whether increased FgF10 levels after myocardial infarction would protect cardiac function, the temporal conditional overexpression of Fgf0 was achieved using the Rosa26-RTTA Tet(O)-Fgf10 mouse line treated with Doxycycline one days after myocardial infarction. The analysis cardiac function 3 weeks post-MI using echocardiographic measurement reveealed that Fgf0 upregulation is sufficient to improve cardiac function post-MI (FIG. 12).

Altogether these results show that FGF10 is required to preserve cardiac function and remodeling following myocardial infarction and support the fact that FGF10 is thus a clinically relevant target for heart regeneration.

Example 2

Material and Methods

Quantitative Real Time PCR on human samples. Total RNA was extracted using Trizol LS reagent (Life technologies). First strand cDNA was synthesized using Maxima Reverse Transcriptase (Life technologies). qRT-PCR was performed using the following primers and Luminaris qPCR SuperMix (Life technologies) and a Roche Light Cycler 480. Each experiment was performed in duplicate and normalized to PPIA and YWHAZ. Quantitative RT-PCR primers are the following:

```
COL1A2-F
                                    (SEQ ID NO: 31)
CTCGCTCAGCACCTTCTCTC,

COL1A2-R
                                    (SEQ ID NO: 32)
CACTCTGGGTGGCTGAGTC,

FGF10-F
                                    (SEQ ID NO: 33)
GAAGGAGAACTGCCCGTACA,

FGF10-R
                                    (SEQ ID NO: 34)
GGCAACAACTCCGATTTCTACT,

PPIA-F
                                    (SEQ ID NO: 35)
ATGCTGGACCCAACACAAAT,

PPIA-R
                                    (SEQ ID NO: 36)
TCTTTCACTTTGCCAAACACC,

YWHAZ-F
                                    (SEQ ID NO: 37)
GTGGACATCGGATACCCAAG,

YWHAZ-R
                                    (SEQ ID NO: 38)
AAGTTGGAAGGCCGGTTAAT.
```

Results

In order to determine whether increased FgF10 levels after myocardial infarction would protect cardiac function, the temporal conditional overexpression of Fgf10 was achieved using the Rosa26-RTTA Tet(O)-Fgf10 mouse line treated with Doxycycline one day after myocardial infarction MI). The analysis of cardiac function 3 weeks post-MI using echocardiographic measurement revealed that Fgf0 upregulation is sufficient to preserve cardiac function and remodeling post-MI (FIGS. 13A-C). These results thus confirm those presented in FIG. 12.

How FGF10 would be protective upon myocardial infarction was then investigated by analyzing cardiac cell proliferation in R26R-RTTA Tet(O)-Fgf10-MI mice treated with CTRL or DOX food, three weeks (FIG. 14). Immunofluorescence analysis of the proliferative capacities, using the pan-cell cycle marker Ki-67 (FIG. 14A) and, the cytokinesis marker Aurora B (FIG. 14B), revealed that upregulated Fgf0 levels post-MI promotes cardiomyocyte proliferation. In addition, cardiomyocyte cross sectional area measurement (FIG. 14C) revealed decreased cardiomyocyte cell size in R26R-RTTA Tet(O)-Fgf10-MI mice treated with DOX food compare to R26R-RTTA Tet(O)-Fgf10-MI mice treated with CTRL food, strongly reinforcing the pro-proliferative effect of FGF10 on cardiomyocytes post-MI.

Histological analysis using sirius red staining was then performed to determine the impact of Fgf10 upregulation levels on the progression of cardiac fibrosis following MI. Three weeks post-MI decreased fibrosis infiltration was observed in the hearts from R26R-RTTA Tet(O)-Fgf10-MI mice treated with DOX food compare to R26R-RTTA Tet(O)-Fgf10-MI mice treated with CTRL food (FIGS. 15A and B) correlating with downregulated Col6A5 gene expression (FIG. 15C).

Altogether these results show that FGF10 is required to preserve cardiac function and remodeling following myocardial infarction and support the fact that FGF10 is thus a clinically relevant target for heart regeneration.

We then investigated FGF10 expression levels in human failing explanted heart samples. Our results revealed that elevated levels of FGF10 are observed in the border zone (BZ; 3 out of 6 patients) and the infarcted area (IA; 4 out of 6 patients) of patients with terminal heart failure (FIG. 16A). Immunofluorescence experiments using the pan-cell cycle marker Ki-67 and WGA staining, revealed that, in both areas, FGF10 elevated levels strongly correlate with enhanced cardiomyocyte proliferation (FIGS. 16B and C) and decreased cardiomyocyte cell size (FIG. 17). In addition, histological analysis using sirius red staining (FIG. 18A) and qRT-PCR experiments (FIG. 18B) demonstrated that FGF10 elevated levels strongly correlate with reduced fibrosis infiltration.

Altogether these results strongly demonstrate the regenerative capacities of FGF10 and support the fact that FGF10 might be a clinically relevant target for heart regeneration in Human.

The invention claimed is:

1. A method for promoting cardiomyocyte proliferation to enhance cardiac regeneration in a subject suffering from a heart disease selected from myocardial infarction, ischemic heart disease, heart fibrosis and congestive heart failure, comprising administering to said subject a therapeutically effective amount of a FGF10 protein.

2. The method according to claim 1, wherein the heart disease is myocardial infarction.

3. The method according to claim 1, wherein the FGF10 protein is administered via the oral, intramuscular, subcutaneous, intraperitoneal route, intracardiac or intravascular route.

4. The method according to claim 1, wherein the FGF10 protein is administered into the vasculature or into the heart.

5. The method according to claim 4, wherein the FGF10 protein is administered acutely or chronically.

6. The method according to claim 1, wherein the FGF10 protein is administered daily from the day of myocardial infarction or from the day the subject suffering from a heart disease selected from myocardial infarction, ischemic heart disease, heart fibrosis and congestive heart failure is provided medical care for said heart disease, or from the day the subject suffering from a heart disease selected from myocardial infarction, ischemic heart disease, heart fibrosis and congestive heart failure is diagnosed with said heart disease.

7. The method according to claim 6, wherein the FGF10 protein is administered daily from the day of myocardial infarction.

8. The method according to claim 6, wherein the FGF10 protein is administered daily from the day the subject suffering from a heart disease selected from myocardial infarction, ischemic heart disease, heart fibrosis and congestive heart failure is provided medical care for said heart disease.

9. The method according to claim 6, wherein the FGF10 protein is administered daily from the day the subject suffering from a heart disease selected from myocardial infarction, ischemic heart disease, heart fibrosis and congestive heart failure is diagnosed with said heart disease.

10. The method according to claim 1, wherein the heart disease is ischemic heart disease.

11. The method according to claim 1, wherein the heart disease is heart fibrosis.

12. The method according to claim 1, wherein the heart disease is congestive heart failure.

* * * * *

UNITED STATES PATENT AND TRADEMARK OFFICE
CERTIFICATE OF CORRECTION

Page 1 of 2

PATENT NO. : 12,064,470 B2
APPLICATION NO. : 16/764043
DATED : August 20, 2024
INVENTOR(S) : Francesca Nadège Joëlle Rochais It is certified that error appears in the above-identified patent and that said Letters Patent is hereby corrected as shown below:

In the Specification

Column 3,
Line 60, "Co3A1" should read --Col3A1--.

Column 4,
Line 14, "Fgf0" should read --Fgf10--.
Line 22, "Fgf0" should read --Fgf10--.
Line 41, "Fgf0" should read --Fgf10--.

Column 5,
Line 29, "015520)." should read --O15520).--.

Column 9,
Line 9, "Fgf0" should read --Fgf10--.

Column 12,
Line 61, "Fgf0" should read --Fgf10--.

Column 13,
Line 1, "Fgf0" should read --Fgf10--.
Line 5, "Fgf0" should read --Fgf10--.
Line 7, "Fgf0" should read --Fgf10--.
Line 11, "Fgf0" should read --Fgf10--.
Line 17, "Fgf0" should read --Fgf10--.
Line 56, "Fgf0" should read --Fgf10--.

Column 14,
Line 9, "Fgf0" should read --Fgf10--.
Line 17, "Fgf0" should read --Fgf10--.

Signed and Sealed this
Twenty-first Day of October, 2025

John A. Squires
*Director of the United States Patent and Trademark Office*

CERTIFICATE OF CORRECTION (continued)
U.S. Pat. No. 12,064,470 B2

Line 21, "Fgf0" should read --Fgf10--.

Column 15,
Line 8, "Fgf0" should read --Fgf10--.
Line 18, "Fgf0" should read --Fgf10--.